United States Patent [19]

Huang et al.

[11] Patent Number: 5,672,626
[45] Date of Patent: Sep. 30, 1997

[54] SUBSTITUTED SPIRODIENES FOR THE TREATMENT OF INFLAMMATION

[75] Inventors: Horng-Chih Huang; David R. Reitz, both of Chesterfield, Mo.

[73] Assignee: G. D. Searle & Co., Skokie, Ill.

[21] Appl. No.: 674,700

[22] Filed: Jul. 9, 1996

Related U.S. Application Data

[62] Division of Ser. No. 237,739, May 4, 1994, abandoned.

[51] Int. Cl.⁶ .............. A61K 31/275; C07C 255/49; C07C 307/02; C07C 317/14
[52] U.S. Cl. .............. 514/520; 514/604; 514/708; 514/709; 558/413; 564/85; 564/89; 564/90; 568/27; 568/29; 568/32; 568/33; 568/35
[58] Field of Search .............. 558/413; 564/85, 564/89, 90; 568/29, 32, 33, 35; 514/520, 604, 708, 709

[56] References Cited

U.S. PATENT DOCUMENTS 4,946,993  8/1990  Cortes .............. 562/17

OTHER PUBLICATIONS

T. Hla and K. Neilson, *Proc. Natl. Acad. Sci. USA*, 89, 7384–7388 (1992).
J.L. Masferrer et al, *Proc. Natl. Acad. Sci. USA*, 89, 3917 (1992).
E. Meade et al, *J. Biol. Chem.*, 268, 6610 (1993).
N. Futaki et al, *Prostaglandins*, 47, 1 (1994).
C. Allen et al, *J. Org. Chem.*, 11, 268 (1946).

H. Zimmerman and J. Pincock, *J. Amer. Chem. Soc.*, 95, 3246 (1973).
K. Hirao et al, *J. Chem. Soc., Chem. Commun.*, 300 (1984).
M. Hamer and Stubs, *J. Chem. Soc., D*, 1013 (1970).

*Primary Examiner*—Alan L. Rotman
*Attorney, Agent, or Firm*—Joseph W. Bulock

[57] ABSTRACT

A class of substituted spirodienes is described for use in treating inflammation and inflammation-related disorders. Compounds of particular interest are defined by Formula II:

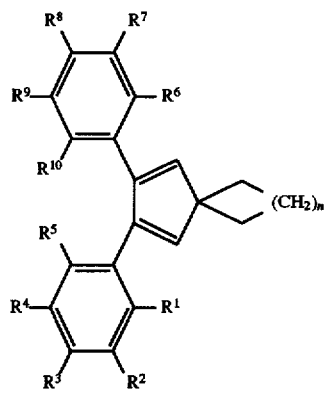

wherein each of $R^1$, $R^2$, $R^4$ and $R^5$ is hydrido; wherein $R^3$ is methylsulfonyl or sulfamyl; and wherein each of $R^6$ through $R^{10}$ is independently selected from hydrido, halo, alkyl, alkoxy, alkylthio, cyano, haloalkyl, haloalkoxy, hydroxyalkyl, alkoxyalkyl, hydroxyl, and mercapto; and wherein n is 1, 2 or 3; or a pharmaceutically-acceptable salt thereof.

18 Claims, No Drawings

SUBSTITUTED SPIRODIENES FOR THE TREATMENT OF INFLAMMATION

RELATED CASES

This is a divisional application of U.S. patent application Ser. No. 08/237,739, filed on May 4, 1994, now abandoned.

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). Recently, the sequence of a previously unknown enzyme in the human arachidonic acid/prostaglandin pathway has been reported by T. Hla and K. Nielson, *Proc. Natl. Acad. Sci, USA*, 89, 7384 (1992) and named "cyclooxygenase II (COX II)" or "prostaglandin G/H synthase II." The discovery of an inducible enzyme associated with inflammation provides a viable target of inhibition which more effectively reduces inflammation and produces fewer and less drastic side effects. Cyclooxygenase II is inducible by cytokines or endotoxins and such induction is inhibited by glucocortoids (J. Masferrer, et al, *Proc. Natl. Acad. Sci, USA*, 89, 3917 (1992)). The 6-methoxy-2-napthylacetic acid metabolite of nabumetone has been found by E. Meade et al to selectively inhibit the COX II enzyme (*J. Biol. Chem.*, 268, 6610 (1993)). In addition, Futaki et al (Prostaglandisn, 47, 55 (1994)) have reported that N-(2-cyclohexyloxy-4-nitrophenyl)methanesulfonamide inhibits cyclooxygenase II and lacks gastric side effects.

The substituted spiro compounds disclosed herein selectively inhibit cyclooxygenase II over cyclooxygenase I and relieve the effects of inflammation. These compounds, in addition, do not display substantial inhibition of cyclooxygenase I and produce a reduced amount of side effects.

Substituted spiro compounds are described in a copending application Ser. No. 08/194,762.

U.S. Pat. No. 4,946,993 to Cortes, describes the use of aryl substituted cyclopentadienes to form N-phosphonomethylglycine.

Allen et al [*J. Org. Chem.*, 11, 268 (1946)] describe the formation of 3,4-diphenylcyclopentadiene.

Zimmerman and Pinock [*J. Amer. Chem. Soc.*, 95, 3246 (1973)] describe the synthesis of 5,5-dimethyl-2,3-diphenylcyclopentadiene from diacetylenic compounds.

Hirao et al [*J. Chem. Soc., Chem. Commun.*, 300 (1984)] describe the synthesis of norbornadienes from substituted cyclopentadienes and acetylenes. Specifically, 1,1'-(4,4-dimethyl-2,5-cyclopentadien-1,2-diyl)bis[4-methoxybenzene] is described.

Hamer and Stubbs [*J. Chem. Soc., D*, 1013 (1970)] describe the formation of spiro[2,4]hepta-4,6-dienes through the photoisomerization of bicyclo[3,1,0]hex-2-enes. Specifically, 1,5,6-triphenylspiro[2,4]hepta-4,6-diene is described.

DESCRIPTION OF THE INVENTION

A class of substituted spiro compounds useful in treating inflammation-related disorders is defined by Formula I:

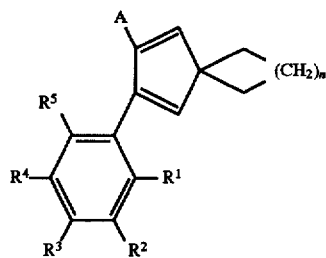

wherein A is selected from

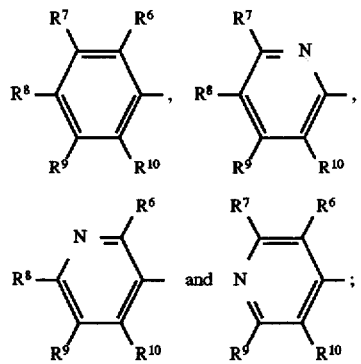

wherein each of $R^1$ through $R^{10}$ is independently selected from hydrido, halo, alkyl, alkoxy, alkylthio, cyano, haloalkyl, haloalkoxy, hydroxyalkyl, alkoxyalkyl, hydroxyl, mercapto, alkylsulfonyl, haloalkylsulfonyl and sulfamyl; and wherein n is a number selected from 0, 1, 2 and 3; or a pharmaceutically-acceptable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel syndrome, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as anti-inflammatory agents, such as for the treatment of arthritis, with the additional benefit of having significantly less harmful side effects.

The present invention also includes compounds which selectively inhibit cyclooxygenase II over cyclooxygenase I and do not significantly inhibit one or more other arachidonic pathway steps, such as thromboxane $B_2$ ($TXB_2$) production. Importantly, thromboxanes cause blood platelet aggregation and have vasoconstriction properties. Thus a lack of effect in the regulation of non-inflammation related thromboxane production is further evidence of the beneficial selectivity of the present compounds.

Preferably, the compounds have a cyclooxygenase II $IC_{50}$ less than about 0.1 μM, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 0.5 μM, and more preferably of greater than 5 μM. Such preferred selectivity may indicate an ability to reduce the incidence of common NSAID-induced side effects, such as ulcers.

A preferred class of compounds consists of those compounds of Formula I wherein each of $R^1$ through $R^{10}$ is independently selected from hydrido, halo, lower alkyl, lower alkoxy, lower alkylthio, cyano, lower haloalkyl, lower haloalkoxy, lower hydroxyalkyl, lower alkoxyalkyl, hydroxyl, mercapto, lower alkylsulfonyl, lower haloalkylsulfonyl and sulfamyl; or a pharmaceutically-acceptable salt thereof.

A class of compounds of particular interest consists of those compounds of Formula I wherein each of $R^1$ through $R^{10}$ is independently selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl, ethoxymethyl, methylsulfonyl, fluoromethylsulfonyl, difluoromethylsulfonyl, trifluoromethylsulfonyl and sulfamyl; or a pharmaceutically-acceptable salt thereof.

Within Formula I there is a subclass of compounds of high interest represented by Formula II:

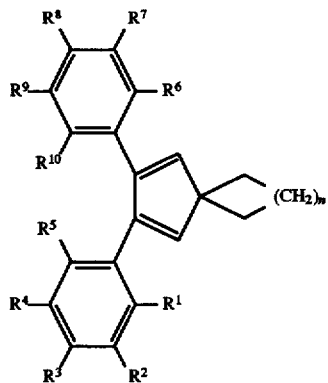

wherein each of $R^1$ through $R^{10}$ is independently selected from hydrido, halo, alkyl, alkoxy, alkylthio, cyano, haloalkyl, haloalkoxy, hydroxyalkyl, alkoxyalkyl, hydroxyl, mercapto, alkylsulfonyl, haloalkylsulfonyl and sulfamyl; and wherein n is a number selected from 0, 1, 2 and 3; or a pharmaceutically-acceptable salt thereof.

A preferred class of compounds consists of those compounds of Formula II wherein n is a number selected from 0, 1 and 2; wherein each of $R^1$ through $R^{10}$ is independently selected from hydrido, halo, lower alkyl, lower alkylthio, cyano, lower haloalkyl, lower haloalkoxy, lower alkoxy, hydroxyl, mercapto, lower hydroxyalkyl, lower alkoxyalkyl, lower alkylsulfonyl, lower haloalkylsulfonyl and sulfamyl; or a pharmaceutically-acceptable salt thereof.

A class of compounds of particular interest consists of those compounds of Formula II wherein each of $R^1$ through $R^{10}$ is independently selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl, ethoxymethyl, methylsulfonyl, fluoromethylsulfonyl, difluoromethylsulfonyl, trifluoromethylsulfonyl and sulfamyl; or a pharmaceutically-acceptable salt thereof.

A family of specific compounds of particular interest within Formula II consists of compounds and pharmaceutically-acceptable salts thereof as follows:

5-phenyl-6-[4-(methylsulfonyl)phenyl]spiro[2.4]hepta-4,6-diene;

5-(4-fluorophenyl)-6-[4-(methylsulfonyl)phenyl]spiro[2.4]hepta-4,6-diene;

5-(4-chlorophenyl)-6-[4-(methylsulfonyl)phenyl]spiro [2.4]hepta-4,6-diene;

5-(4-bromophenyl)-6-[4-(methylsulfonyl)phenyl]spiro [2.4]hepta-4,6-diene;

5-(4-iodophenyl)-6-[4-(methylsulfonyl)phenyl]spiro [2.4]hepta-4,6-diene;

5-(4-methylphenyl)-6-[4-(methylsulfonyl)phenyl]spiro [2.4]hepta-4,6-diene;

5-(4-ethylphenyl)-6-[4-(methylsulfonyl)phenyl]spiro [2.4]hepta-4,6-diene;

5-(4-methoxyphenyl)-6-[4-(methylsulfonyl) phenyl]spiro [2.4]hepta-4,6-diene;

5-(4-methylthiophenyl)-6-[4-(methylsulfonyl)phenyl]spiro [2.4]hepta-4,6-diene;

5-(4-cyanophenyl)-6-[4-(methylsulfonyl)phenyl]spiro [2.4]hepta-4,6-diene;

5-(4-trifluoromethylphenyl)-6-[4-(methylsulfonyl) phenyl] spiro[2.4]hepta-4,6-diene;

5-(4-hydroxymethylphenyl)-6-[4-(methylsulfonyl) phenyl] spiro[2.4]hepta-4,6-diene;

5-(4-methoxymethylphenyl)-6-[4-(methylsulfonyl) phenyl] spiro[2.4]hepta-4,6-diene;

5-(4-hydroxyphenyl)-6-[4-(methylsulfonyl) phenyl]spiro [2.4]hepta-4,6-diene;

5-(4-mercaptophenyl)-6-[4-(methylsulfonyl) phenyl]spiro [2.4]hepta-4,6-diene;

4-(6-phenylspiro[2.4]hepta-4,6-dien-5-yl) benzenesulfonamide;

4-[6-(4-fluorophenyl)spiro[2.4]hepta-4,6-dien-5-yl] benzenesulfonamide;

4-[6-(4-chlorophenyl)spiro[2.4]hepta-4,6-dien-5-yl] benzenesulfonamide;

4-[6-(4-bromophenyl)spiro[2.4]hepta-4,6-dien-5-yl] benzenesulfonamide;

4-[6-(4-iodophenyl)spiro[2.4]hepta-4,6-dien-5-yl] benzenesulfonamide;

4-[6-(4-methylphenyl)spiro[2.4]hepta-4,6-dien-5-yl] benzenesulfonamide;

4-[6-(4-ethylphenyl)spiro[2.4]hepta-4,6-dien-5-yl] benzenesulfonamide;
4-[6-(4-methoxyphenyl)spiro[2.4]hepta-4,6-dien-5-yl] benzenesulfonamide;
4-[6-(4-methylthiophenyl)spiro[2.4]hepta-4,6-dien-5-yl] benzenesulfonamide;
4-[6-(4-cyanophenyl)spiro[2.4]hepta-4,6-diet-5-yl] benzenesulfonamide;
4-[6-(4-trifluoromethylphenyl)spiro[2.4]hepta-4,6-dien-5-yl]benzenesulfonamide;
4-[6-(4-hydroxymethylphenyl)spiro[2.4]hepta-4,6-dien-5-yl]benzenesulfonamide;
4-[6-(4-methoxymethylphenyl)spiro[2.4]hepta-4,6-dien-5-yl]benzenesulfonamide;
4-[6-(4-hydroxyphenyl)spiro[2.4]hepta-4,6-dien-5-yl] benzenesulfonamide;
4-[6-(4-mercaptophenyl)spiro[2.4]hepta-4,6-dien-5-yl] benzenesulfonamide;
6-phenyl-7-[4-(methylsulfonyl)phenyl]spiro[3.4]octa-5,7-diene;
6-(4-fluorophenyl)-7-[4-(methylsulfonyl)phenyl]spiro[3.4]octa-5,7-diene;
6-(4-chlorophenyl)-7-[4-(methylsulfonyl)phenyl]spiro[3.4]octa-5,7-diene;
6-(4-bromophenyl)-7-[4-(methylsulfonyl)phenyl]spiro[3.4]octa-5,7-diene;
6-(4-iodophenyl)-7-[4-(methylsulfonyl)phenyl]spiro[3.4]octa-5,7-diene;
6-(4-methylphenyl)-7-[4-(methylsulfonyl)phenyl]spiro[3.4]octa-5,7-diene;
6-(4-ethylphenyl)-7-[4-(methylsulfonyl)phenyl]spiro[3.4]octa-5,7-diene;
6-(4-methoxyphenyl)-7-[4-(methylsulfonyl)phenyl]spiro[3.4]octa-5,7-diene;
6-(4-methylthiophenyl)-7-[4-(methylsulfonyl)phenyl]spiro[3.4]octa-5,7-diene;
6-(4-cyanophenyl)-7-[4-(methylsulfonyl)phenyl]spiro[3.4]octa-5,7-diene;
6-(4-trifluoromethylphenyl)-7-[4-(methylsulfonyl) phenyl]spiro[3.4]octa-5,7-diene;
6-(4-hydroxymethylphenyl)-7-[4-(methylsulfonyl) phenyl]spiro[3.4]octa-5,7-diene;
6-(4-methoxymethylphenyl)-7-[4-(methylsulfonyl) phenyl]spiro[3.4]octa-5,7-diene;
6-(4-hydroxyphenyl)-7-[4-(methylsulfonyl)phenyl]spiro[3.4]octa-5,7-diene;
6-(4-mercaptophenyl)-7-[4-(methylsulfonyl)phenyl]spiro[3.4]octa-5,7-diene;
4-(7-phenylspiro[3.4]octa-5,7-dien-6-yl) benzenesulfonamide;
4-[7-(4-fluorophenyl)spiro[3.4]octa-5,7-dien-6-yl] benzenesulfonamide;
4-[7-(4-chlorophenyl)spiro[3.4]octa-5,7-dien-6-yl] benzenesulfonamide;
4-[7-(4-bromophenyl)spiro[3.4]octa-5,7-dien-6-yl] benzenesulfonamide;
4-[7-(4-iodophenyl)spiro[3.4]octa-5,7-dien-6-yl] benzenesulfonamide;
4-[7-(4-methylphenyl)spiro[3.4]octa-5,7-dien-6-yl] benzenesulfonamide;
4-[7-(4-ethylphenyl)spiro[3.4]octa-5,7-dien-6-yl] benzenesulfonamide;
4-[7-(4-methoxyphenyl)spiro[3.4]octa-5,7-dien-6-yl] benzenesulfonamide;
4-[7-(4-methylthiophenyl)spiro[3.4]octa-5,7-dien-6-yl] benzenesulfonamide;
4-[7-(4-cyanophenyl)spiro[3.4]octa-5,7-dien-6-yl] benzenesulfonamide;
4-[7-(4-trifluoromethylphenyl)spiro[3.4]octa-5,7-dien-6-yl] benzenesulfonamide;
4-[7-(4-hydroxymethylphenyl)spiro[3.4]octa-5,7-dien-6-yl] benzenesulfonamide;
4-[7-(4-methoxymethylphenyl)spiro[3.4]octa-5,7-dien-6-yl] benzenesulfonamide;
4-[7-(4-hydroxyphenyl)spiro[3.4]octa-5,7-dien-6-yl] benzenesulfonamide;
4-[7-(4-mercaptophenyl)spiro[3.4]octa-5,7-dien-6-yl] benzenesulfonamide;
2-phenyl-3-[4-(methylsulfonyl)phenyl]spiro[4.4]nona-1,3-diene;
2-(4-fluorophenyl)-3-[4-(methylsulfonyl)phenyl]spiro[4.4]nona-1,3-diene;
2-(4-chlorophenyl)-3-[4-(methylsulfonyl)phenyl]spiro[4.4]nona-1,3-diene;
2-(4-bromophenyl)-3-[4-(methylsulfonyl)phenyl]spiro[4.4]nona-1,3-diene;
2-(4-iodophenyl)-3-[4-(methylsulfonyl)phenyl]spiro[4.4]nona-1,3-diene;
2-(4-methylphenyl)-3-[4-(methylsulfonyl)phenyl]spiro[4.4]nona-1,3-diene;
2-(4-ethylphenyl)-3-[4-(methylsulfonyl)phenyl]spiro[4.4]nona-1,3-diene;
2-(4-methoxyphenyl)-3-[4-(methylsulfonyl)phenyl]spiro[4.4]nona-1,3-diene;
2-(4-methylthiophenyl)-3-[4-(methylsulfonyl)phenyl]spiro[4.4]nona-1,3-diene;
2-(4-cyanophenyl)-3-[4-(methylsulfonyl)phenyl]spiro[4.4]nona-1,3-diene;
2-(4-trifluoromethylphenyl)-3-[4-(methylsulfonyl) phenyl]spiro[4.4]nona-1,3-diene;
2-(4-hydroxymethylphenyl)-3-[4-(methylsulfonyl) phenyl]spiro[4.4]nona-1,3-diene;
2-(4-methoxymethylphenyl)-3-[4-(methylsulfonyl) phenyl]spiro[4.4]nona-1,3-diene;
2-(4-hydroxyphenyl)-3-[4-(methylsulfonyl)phenyl]spiro[4.4]nona-1,3-diene;
2-(4-mercaptophenyl)-3-[4-(methylsulfonyl)phenyl]spiro[4.4]nona-1,3-diene;
4-(3-phenylspiro[4.4]nona-1,3-dien-2-yl) benzenesulfonamide;
4-[3-(4-fluorophenyl)spiro[4.4]nona-1,3-dien-2-yl] benzenesulfonamide;
4-[3-(4-chlorophenyl)spiro[4.4]nona-1,3-dien-2-yl] benzenesulfonamide;
4-[3-(4-bromophenyl)spiro[4.4]nona-1,3-dien-2-yl] benzenesulfonamide;
4-[3-(4-iodophenyl)spiro[4.4]nona-1,3-dien-2-yl] benzenesulfonamide;
4-[3-(4-methylphenyl)spiro[4.4]nona-1,3-dien-2-yl] benzenesulfonamide;
4-[3-(4-ethylphenyl)spiro[4.4]nona-1,3-dien-2-yl] benzenesulfonamide;
4-[3-(4-methoxyphenyl)spiro[4.4]nona-1,3-dien-2-yl] benzenesulfonamide;
4-[3-(4-methylthiophenyl)spiro[4.4]nona-1,3-dien-2-yl] benzenesulfonamide;
4-[3-(4-cyanophenyl)spiro[4.4]nona-1,3-dien-2-yl] benzenesulfonamide;
4-[3-(4-trifluoromethylphenyl)spiro[4.4]nona-1,3-dien-2-yl]benzenesulfonamide;
4-[3-(4-hydroxymethylphenyl)spiro[4.4]nona-1,3-dien-2-yl]benzenesulfonamide;
4-[3-(4-methoxymethylphenyl)spiro[4.4]nona-1,3-dien-2-yl]benzenesulfonamide;
4-[3-(4-hydroxyphenyl)spiro[4.4]nona-1,3-dien-2-yl] benzenesulfonamide;

4-[3-(4-mercaptophenyl)spiro[4.4]nona-1,3-dien-2-yl] benzenesulfonamide;

5-(3-trifluoromethyl-4-methylphenyl)-6-[4-(methylsulfonyl)phenyl]spiro[2.4]hepta-4,6-diene;

5-(3-trifluoromethyl-4-fluorophenyl)-6-[4-(methylsulfonyl) phenyl]spiro[2.4]hepta-4,6-diene;

5-(3-trifluoromethyl-4-chlorophenyl)-6-[4-(methylsulfonyl) phenyl]spiro[2.4]hepta-4,6-diene;

5-(3-trifluoromethyl-4-bromophenyl)-6-[4-(methylsulfonyl) phenyl]spiro[2.4]hepta-4,6-diene;

5-(3-methyl-4-fluorophenyl)-6-[4-(methylsulfonyl) phenyl]spiro[2.4]hepta-4,6-diene;

5-(3-methyl-4-chlorophenyl)-6-[4-(methylsulfonyl) phenyl]spiro[2.4]hepta-4,6-diene;

5-(3-methyl-4-bromophenyl)-6-[4-(methylsulfonyl) phenyl]spiro[2.4]hepta-4,6-diene;

5-(3-methyl-4-trifluorophenyl)-6-[4-(methylsulfonyl) phenyl]spiro[2.4]hepta-4,6-diene;

5-(3-trifluoromethyl-4-methoxyphenyl)-6-[4-(methylsulfonyl)phenyl]spiro[2.4]hepta-4,6-diene;

5-(3-methyl-4-methoxyphenyl)-6-[4-(methylsulfonyl) phenyl]spiro[2.4]hepta-4,6-diene;

5-(3-fluoro-4-methoxyphenyl)-6-[4-(methylsulfonyl) phenyl]spiro[2.4]hepta-4,6-diene;

5-(3-chloro-4-methoxyphenyl)-6-[4-(methylsulfonyl) phenyl]spiro[2.4]hepta-4,6-diene;

5-(3-bromo-4-methoxyphenyl)-6-[4-(methylsulfonyl) phenyl]spiro[2.4]hepta-4,6-diene;

5-(2,3,4,5,6-pentafluorophenyl)-6-[4-(methylsulfonyl) phenyl]spiro[2.4]hepta-4,6-diene;

5-(4-methoxy-2,3,5,6-tetrafluorophenyl)-6-[4-(methylsulfonyl)phenyl]spiro[2.4]hepta-4,6-diene;

5-(2,3,5,6-tetrafluoro-4-trifluoromethylphenyl)-6-[4-(methylsulfonyl) phenyl]spiro[2.4]hepta-4,6-diene;

5-(3,5-difluoro-4-methoxyphenyl)-6-[4-(methylsulfonyl) phenyl]spiro[2.4]hepta-4,6-diene;

5-(3,5-dichloro-4-methyoxyphenyl)-6-[4-(methylsulfonyl) phenyl]spiro[2.4]hepta-4,6-diene;

5-(3,5-dibromo-4-methoxyphenyl)-6-[4-(methylsulfonyl) phenyl]spiro[2.4]hepta-4,6-diene;

5-(2,3,4-trifluoro-4-methoxyphenyl)-6-[4-(methylsulfonyl) phenyl]spiro[2.4]hepta-4,6-diene;

5-(2,3,4-trichloro-4-methoxyphenyl)-6-[4-(methylsulfonyl) phenyl]spiro[2.4]hepta-4,6-diene;

5-(2,3,4-tribromo-4-methoxyphenyl)-6-[4-(methylsulfonyl) phenyl]spiro[2.4]hepta-4,6-diene;

5-(2,4,5-trifluoro-4-methoxyphenyl)-6-[4-(methylsulfonyl) phenyl]spiro[2.4]hepta-4,6-diene;

5-(2,4,5-trichloro-4-methoxyphenyl)-6-[4-(methylsulfonyl) phenyl]spiro[2.4]hepta-4,6-diene;

5-(2,4,5-tribromo-4-methoxyphenyl)-6-[4-(methylsulfonyl) phenyl]spiro[2.4]hepta-4,6-diene;

5-(3,4-dimethoxyphenyl)-6-[4-(methylsulfonyl)phenyl] spiro[2.4]hepta-4,6-diene;

5-(3,4,5-trimethoxyphenyl)-6-[4-(methylsulfonyl)phenyl] spiro[2.4]hepta-4,6-diene;

5-[3,4-bis (trifluoromethyl)phenyl]-6-[4-(methylsulfonyl) phenyl]spiro[2.4]hepta-4,6-diene;

5-(3,4-dimethylphenyl)-6-[4-(methylsulfonyl)phenyl]spiro [2.4]hepta-4,6-diene;

5-(3,4-difluorophenyl)-6-[4-(methylsulfonyl)phenyl]spiro [2.4]hepta-4,6-diene;

5-(3,4-dichlorophenyl)-6-[4-(methylsulfonyl)phenyl]spiro [2.4]hepta-4,6-diene;

5-(3,4-dibromophenyl)-6-[4-(methylsulfonyl)phenyl]spiro [2.4]hepta-4,6-diene;

5-(3-chloro-4-fluorophenyl)-6-[4-(methylsulfonyl)phenyl] spiro[2.4]hepta-4,6-diene;

5-(3-chloro-4-bromophenyl)-6-[4-(methylsulfonyl)phenyl] spiro[2.4]hepta-4,6-diene;

5-(4-chloro-3-fluorophenyl)-6-[4-(methylsulfonyl) phenyl] spiro[2.4]hepta-4,6-diene;

5-(4-chloro-3-bromophenyl)-6-[4-(methylsulfonyl)phenyl] spiro[2.4]hepta-4,6-diene;

5-(3-trifluoromethyl-4-methylphenyl)-6-[4-(fluoromethylsulfonyl)phenyl]spiro[2.4]hepta-4,6-diene;

5-(3-trifluoromethyl-4-fluorophenyl)-6-[4-(fluoromethylsulfonyl)phenyl]spiro[2.4]hepta-4,6-diene;

5-(3-trifluoromethyl-4-chlorophenyl)-6-[4-(fluoromethylsulfonyl)phenyl]spiro[2.4]hepta-4,6-diene;

5-(3-trifluoromethyl-4-bromophenyl)-6-[4-(fluoromethylsulfonyl)phenyl]spiro[2.4]hepta-4,6-diene;

5-(3-methyl-4-fluorophenyl)-6-[4-(fluoromethylsulfonyl) phenyl]spiro[2.4]hepta-4,6-diene;

5-(3-methyl-4-chlorophenyl)-6-[4-(fluoromethylsulfonyl) phenyl]spiro[2.4]hepta-4,6-diene;

5-(3-methyl-4-bromophenyl)-6-[4-(fluoromethylsulfonyl) phenyl]spiro[2.4]hepta-4,6-diene;

5-(3-methyl-4-trifluorophenyl)-6-[4-(fluoromethylsulfonyl) phenyl]spiro[2.4]hepta-4,6-diene;

5-(3-trifluoromethyl-4-methoxyphenyl)-6-[4-(fluoromethylsulfonyl)phenyl]spiro[2.4]hepta-4,6-diene;

5-(3-methyl-4-methoxyphenyl)-6-[4-(fluoromethylsulfonyl) phenyl]spiro[2.4]hepta-4,6-diene;

5-(3-fluoro-4-methoxyphenyl)-6-[4-(fluoromethylsulfonyl) phenyl]spiro[2.4]hepta-4,6-diene 5-(3-chloro-4-methoxyphenyl)-6-[4-(fluoromethylsulfonyl) phenyl]spiro[2.4]hepta-4,6-diene;

5-(3-bromo-4-methoxyphenyl)-6-[4-(fluoromethylsulfonyl) phenyl]spiro[2.4]hepta-4,6-diene;

5-(2,3,4,5,6-pentafluorophenyl)-6-[4-(fluoromethylsulfonyl)phenyl]spiro[2.4]hepta-4,6-diene;

5-(4-methoxy-2,3,5,6-tetrafluorophenyl)-6-[4-(fluoromethylsulfonyl)phenyl]spiro[2.4]hepta-4,6-diene;

5-(2,3,5,6-tetrafluoro-4-trifluoromethylphenyl)-6-[4-(fluoromethylsulfonyl)phenyl]spiro[2.4]hepta-4,6-diene;

5-(3,5-difluoro-4-methoxyphenyl)-6-[4-(fluoromethylsulfonyl)phenyl]spiro[2.4]hepta-4,6-diene;

5-(3,5-dichloro-4-methyoxyphenyl)-6-[4-(fluoromethylsulfonyl)phenyl]spiro[2.4]hepta-4,6-diene;

5-(3,5-dibromo-4-methoxyphenyl)-6-[4-(fluoromethylsulfonyl)phenyl]spiro[2.4]hepta-4,6-diene;

5-(2,3,4-trifluoro-4-methoxyphenyl)-6-[4-(fluoromethylsulfonyl)phenyl]spiro[2.4]hepta-4,6-diene;

5-(2,3,4-trichloro-4-methyoxyphenyl)-6-[4-(fluoromethylsulfonyl)phenyl]spiro[2.4]hepta-4,6-diene;

5-(2,3,4-tribromo-4-methyoxyphenyl)-6-[4-(fluoromethylsulfonyl)phenyl]spiro[2.4]hepta-4,6-diene;

5-(2,4,5-trifluoro-4-methoxyphenyl)-6-[4-(fluoromethylsulfonyl)phenyl]spiro[2.4]hepta-4,6-diene;

5-(2,4,5-trichloro-4-methyoxyphenyl)-6-[4-(fluoromethylsulfonyl)phenyl]spiro[2.4]hepta-4,6-diene;

5-(2,4,5-tribromo-4-methyoxyphenyl)-6-[4-(fluoromethylsulfonyl)phenyl]spiro[2.4]hepta-4,6-diene;

5-(3,4-dimethoxyphenyl)-6-[4-(fluoromethylsulfonyl) phenyl]spiro[2.4]hepta-4,6-diene;

5-(3,4,5-trimethoxyphenyl)-6-[4-(fluoromethylsulfonyl) phenyl]spiro[2.4]hepta-4,6-diene;

5-[3,4-bis (trifluoromethyl)phenyl]-6-[4-(fluoromethylsulfonyl)phenyl]spiro[2.4]hepta-4,6-diene;

5-(3,4-dimethylphenyl)-6-[4-(fluoromethylsulfonyl)phenyl] spiro[2.4]hepta-4,6-diene;

5-(3,4-difluorophenyl)-6-[4-(fluoromethylsulfonyl)phenyl] spiro[2.4]hepta-4,6-diene;

5-(3,4-dichlorophenyl)-6-[4-(fluoromethylsulfonyl)phenyl] spiro[2.4]hepta-4,6-diene;

5-(3,4-dibromophenyl)-6-[4-(fluoromethylsulfonyl)phenyl]spiro[2.4]hepta-4,6-diene;

5-(3-chloro-4-fluorophenyl)-6-[4-(fluoromethylsulfonyl)phenyl]spiro[2.4]hepta-4,6-diene;

5-(3-chloro-4-bromophenyl)-6-[4-(fluoromethylsulfonyl)phenyl]spiro[2.4]hepta-4,6-diene;

5-(4-chloro-3-fluorophenyl)-6-[4-(fluoromethylsulfonyl)phenyl]spiro[2.4]hepta-4,6-diene;

5-(4-chloro-3-bromophenyl)-6-[4-(fluoromethylsulfonyl)phenyl]spiro[2.4]hepta-4,6-diene;

5-(3-trifluoromethyl-4-methylphenyl)-6-[4-(difluoromethylsulfonyl)phenyl]spiro[2.4]hepta-4,6-diene;

5-(3-trifluoromethyl-4-fluorophenyl)-6-[4-(difluoromethylsulfonyl)phenyl]spiro[2.4]hepta-4,6-diene;

5-(3-trifluoromethyl-4-chlorophenyl)-6-[4-(difluoromethylsulfonyl)phenyl]spiro[2.4]hepta-4,6-diene;

5-(3-trifluoromethyl-4-bromophenyl)-6-[4-(difluoromethylsulfonyl)phenyl]spiro[2.4]hepta-4,6-diene;

5-(3-methyl-4-fluorophenyl)-6-[4-(difluoromethylsulfonyl)phenyl]spiro[2.4]hepta-4,6-diene;

5-(3-methyl-4-chlorophenyl)-6-[4-(difluoromethylsulfonyl)phenyl]spiro[2.4]hepta-4,6-diene;

5-(3-methyl-4-bromophenyl)-6-[4-(difluoromethylsulfonyl)phenyl]spiro[2.4]hepta-4,6-diene;

5-(3-methyl-4-trifluorophenyl)-6-[4-(difluoromethylsulfonyl)phenyl]spiro[2.4]hepta-4,6-diene;

5-(3-trifluoromethyl-4-methoxyphenyl)-6-[4-(difluoromethylsulfonyl)phenyl]spiro[2.4]hepta-4,6-diene;

5-(3-methyl-4-methoxyphenyl)-6-[4-(difluoromethylsulfonyl)phenyl]spiro[2.4]hepta-4,6-diene;

5-(3-fluoro-4-methoxyphenyl)-6-[4-(difluoromethylsulfonyl)phenyl]spiro[2.4]hepta-4,6-diene;

5-(3-chloro-4-methoxyphenyl)-6-[4-(difluoromethylsulfonyl)phenyl]spiro[2.4]hepta-4,6-diene;

5-(3-bromo-4-methoxyphenyl)-6-[4-(difluoromethylsulfonyl)phenyl]spiro[2.4]hepta-4,6-diene;

5-(2,3,4,5,6-pentafluorophenyl)-6-[4-(difluoromethylsulfonyl)phenyl]spiro[2.4]hepta-4,6-diene;

5-(4-methoxy-2,3,5,6-tetrafluorophenyl)-6-[4-(difluoromethylsulfonyl)phenyl]spiro[2.4]hepta-4,6-diene;

5-(2,3,5,6-tetrafluoro-4-trifluoromethylphenyl)-6-[4-(difluoromethylsulfonyl)phenyl]spiro[2.4]hepta-4,6-diene;

5-(3,5-difluoro-4-methoxyphenyl)-6-[4-(difluoromethylsulfonyl)phenyl]spiro[2.4]hepta-4,6-diene;

5-(3,5-dichloro-4-methyoxyphenyl)-6-[4-(difluoromethylsulfonyl)phenyl]spiro[2.4]hepta-4,6-diene;

5-(3,5-dibromo-4-methoxyphenyl)-6-[4-(difluoromethylsulfonyl)phenyl]spiro[2.4]hepta-4,6-diene;

5-(2,3,4-trifluoro-4-methoxyphenyl)-6-[4-(difluoromethylsulfonyl)phenyl]spiro[2.4]hepta-4,6-diene;

5-(2,3,4-trichloro-4-methyoxyphenyl)-6-[4-(difluoromethylsulfonyl)phenyl]spiro[2.4]hepta-4,6-diene;

5-(2,3,4-tribromo-4-methyoxyphenyl)-6-[4-(difluoromethylsulfonyl)phenyl]spiro[2.4]hepta-4,6-diene;

5-(2,4,5-trifluoro-4-methoxyphenyl)-6-[4-(difluoromethylsulfonyl)phenyl]spiro[2.4]hepta-4,6-diene;

5-(2,4,5-trichloro-4-methyoxyphenyl)-6-[4-(difluoromethylsulfonyl)phenyl]spiro[2.4]hepta-4,6-diene;

5-(2,4,5-tribromo-4-methyoxyphenyl)-6-[4-(difluoromethylsulfonyl)phenyl]spiro[2.4]hepta-4,6-diene;

5-(3,4-dimethoxyphenyl)-6-[4-(difluoromethylsulfonyl)phenyl]spiro[2.4]hepta-4,6-diene;

5-(3,4,5-trimethoxyphenyl)-6-[4-(difluoromethylsulfonyl)phenyl]spiro[2.4]hepta-4,6-diene;

5-[3,4-bis(trifluoromethyl)phenyl]-6-[4-(difluoromethylsulfonyl)phenyl]spiro[2.4]hepta-4,6-diene;

5-(3,4-dimethylphenyl)-6-[4-(difluoromethylsulfonyl)phenyl]spiro[2.4]hepta-4,6-diene;

5-(3,4-difluorophenyl)-6-[4-(difluoromethylsulfonyl)phenyl]spiro[2.4]hepta-4,6-diene;

5-(3,4-dichlorophenyl)-6-[4-(difluoromethylsulfonyl)phenyl]spiro[2.4]hepta-4,6-diene;

5-(3,4-dibromophenyl)-6-[4-(difluoromethylsulfonyl)phenyl]spiro[2.4]hepta-4,6-diene;

5-(3-chloro-4-fluorophenyl)-6-[4-(difluoromethylsulfonyl)phenyl]spiro[2.4]hepta-4,6-diene;

5-(3-chloro-4-bromophenyl)-6-[4-(difluoromethylsulfonyl)phenyl]spiro[2.4]hepta-4,6-diene;

5-(4-chloro-3-fluorophenyl)-6-[4-(difluoromethylsulfonyl)phenyl]spiro[2.4]hepta-4,6-diene;

5-(4-chloro-3-bromophenyl)-6-[4-(difluoromethylsulfonyl)phenyl]spiro[2.4]hepta-4,6-diene;

5-(3-trifluoromethyl-4-methylphenyl)-6-[4-(trifluoromethylsulfonyl)phenyl]spiro[2.4]hepta-4,6-diene;

5-(3-trifluoromethyl-4-fluorophenyl)-6-[4-(trifluoromethylsulfonyl)phenyl]spiro[2.4]hepta-4,6-diene;

5-(3-trifluoromethyl-4-chlorophenyl)-6-[4-(trifluoromethylsulfonyl)phenyl]spiro[2.4]hepta-4,6-diene;

5-(3-trifluoromethyl-4-bromophenyl)-6-[4-(trifluoromethylsulfonyl)phenyl]spiro[2.4]hepta-4,6-diene;

5-(3-methyl-4-fluorophenyl)-6-[4-(trifluoromethylsulfonyl)phenyl]spiro[2.4]hepta-4,6-diene;

5-(3-methyl-4-chlorophenyl)-6-[4-(trifluoromethylsulfonyl)phenyl]spiro[2.4]hepta-4,6-diene;

5-(3-methyl-4-bromophenyl)-6-[4-(trifluoromethylsulfonyl)phenyl]spiro[2.4]hepta-4,6-diene;

5-(3-methyl-4-trifluorophenyl)-6-[4-(trifluoromethylsulfonyl)phenyl]spiro[2.4]hepta-4,6-diene;

5-(3-trifluoromethyl-4-methoxyphenyl)-6-[4-(trifluoromethylsulfonyl)phenyl]spiro[2.4]hepta-4,6-diene;

5-(3-methyl-4-methoxyphenyl)-6-[4-(trifluoromethylsulfonyl)phenyl]spiro[2.4]hepta-4,6-diene;

5-(3-fluoro-4-methoxyphenyl)-6-[4-(trifluoromethylsulfonyl)phenyl]spiro[2.4]hepta-4,6-diene;

5-(3-chloro-4-methoxyphenyl)-6-[4-(trifluoromethylsulfonyl)phenyl]spiro[2.4]hepta-4,6-diene;

5-(3-bromo-4-methoxyphenyl)-6-[4-(trifluoromethylsulfonyl)phenyl]spiro[2.4]hepta-4,6-diene;

5-(2,3,4,5,6-pentafluorophenyl)-6-[4-(trifluoromethylsulfonyl)phenyl]spiro[2.4]hepta-4,6-diene;

5-(4-methoxy-2,3,5,6-tetrafluorophenyl)-6-[4-(trifluoromethylsulfonyl)phenyl]spiro[2.4]hepta-4,6-diene;

5-(2,3,5,6-tetrafluoro-4-trifluoromethylphenyl)-6-[4-(trifluoromethylsulfonyl)phenyl]spiro[2.4]hepta-4,6-diene;

5-(3,5-difluoro-4-methoxyphenyl)-6-[4-(trifluoromethylsulfonyl)phenyl]spiro[2.4]hepta-4,6-diene;

5-(3,5-dichloro-4-methyoxyphenyl)-6-[4-(trifluoromethylsulfonyl)phenyl]spiro[2.4]hepta-4,6-diene;

5-(3,5-dibromo-4-methoxyphenyl)-6-[4-(trifluoromethylsulfonyl)phenyl]spiro[2.4]hepta-4,6-diene;

5-(2,3,4-trifluoro-4-methoxyphenyl)-6-[4-trifluoromethylsulfonyl)phenyl]spiro[2.4]hepta-4,6-diene;

5-(2,3,4-trichloro-4-methyoxyphenyl)-6-[4-trifluoromethylsulfonyl)phenyl]spiro[2.4]hepta-4,6-diene;

5-(2,3,4-tribromo-4-methyoxyphenyl)-6-[4-(trifluoromethylsulfonyl)phenyl]spiro[2.4]hepta-4,6-diene;

5-(2,4,5-trifluoro-4-methoxyphenyl)-6-[4-trifluoromethylsulfonyl)phenyl]spiro[2.4]hepta-4,6-diene;

5-(2,4,5-trichloro-4-methyoxyphenyl)-6-[4-trifluoromethylsulfonyl)phenyl]spiro[2.4]hepta-4,6-diene;

5-(2,4,5-tribromo-4-methyoxyphenyl)-6-[4-trifluoromethylsulfonyl)phenyl]spiro[2.4]hepta-4,6-diene;

5-(3,4-dimethoxyphenyl)-6-[4-(trifluoromethylsulfonyl)phenyl]spiro[2.4]hepta-4,6-diene;

5-(3,4,5-trimethoxyphenyl)-6-[4-(trifluoromethylsulfonyl)phenyl]spiro[2.4]hepta-4,6-diene;

5-[3,4-bis(trifluoromethyl)phenyl]-6-[4-(trifluoromethylsulfonyl)phenyl]spiro[2.4]hepta-4,6-diene;

5-(3,4-dimethylphenyl)-6-[4-(trifluoromethylsulfonyl)phenyl]spiro[2.4]hepta-4,6-diene;

5-(3,4-difluorophenyl)-6-[4-(trifluoromethylsulfonyl)phenyl]spiro[2.4]hepta-4,6-diene;

5-(3,4-dichlorophenyl)-6-[4-(trifluoromethylsulfonyl)phenyl]spiro[2.4]hepta-4,6-diene;

5-(3,4-dibromophenyl)-6-[4-(trifluoromethylsulfonyl)phenyl]spiro[2.4]hepta-4,6-diene;

5-(3-chloro-4-fluorophenyl)-6-[4-(trifluoromethylsulfonyl)phenyl]spiro[2.4]hepta-4,6-diene;

5-(3-chloro-4-bromophenyl)-6-[4-(trifluoromethylsulfonyl)phenyl]spiro[2.4]hepta-4,6-diene;

5-(4-chloro-3-fluorophenyl)-6-[4-(trifluoromethylsulfonyl)phenyl]spiro[2.4]hepta-4,6-diene;

5-(4-chloro-3-bromophenyl)-6-[4-(trifluoromethylsulfonyl)phenyl]spiro[2.4]hepta-4,6-diene;

4-[6-(3-methyl-4-fluorophenyl)spiro[2.4]hepta-4,6-dien-5-yl]benzenesulfonamide;

4-[6-(3-methyl-4-chlorophenyl)spiro[2.4]hepta-4,6-dien-5-yl]benzenesulfonamide;

4-[6-(3-methyl-4-bromophenyl)spiro[2.4]hepta-4,6-dien-5-yl]benzenesulfonamide;

4-[6-(3-methyl-4-trifluoromethylphenyl)spiro[2.4]hepta-4,6-dien-5-yl]benzenesulfonamide;

4-[6-(3-methyl-4-methoxyphenyl)spiro[2.4]hepta-4,6-dien-5-yl]benzenesulfonamide;

4-[6-(3-trifluoromethyl-4-fluorophenyl)spiro[2.4]hepta-4,6-dien-5-yl]benzenesulfonamide;

4-[6-(3-trifluoromethyl-4-chlorophenyl)spiro[2.4]hepta-4,6-dien-5-yl]benzenesulfonamide;

4-[6-(3-trifluoromethyl-4-bromophenyl)spiro[2.4]hepta-4,6-dien-5-yl]benzenesulfonamide;

4-[6-(3-trifluoromethyl-4-methylphenyl)spiro[2.4]hepta-4,6-dien-5-yl]benzenesulfonamide;

4-[6-(3-trifluoromethyl-4-methoxyphenyl)spiro[2.4]hepta-4,6-dien-5-yl]benzenesulfonamide;

4-[6-(3-fluoro-4-methoxyphenyl)spiro[2.4]hepta-4,6-dien-5-yl]benzenesulfonamide;

4-[6-(3-chloro-4-methoxyphenyl)spiro[2.4]hepta-4,6-dien-5-yl]benzenesulfonamide;

4-[6-(3-bromo-4-methoxyphenyl)spiro[2.4]hepta-4,6-dien-5-yl]benzenesulfonamide;

4-[6-(2,3,4,5,6-pentafluorophenyl)spiro[2.4]hepta-4,6-dien-5-yl]benzenesulfonamide;

4-[6-(4-methoxy-2,3,5,6-tetrafluorophenyl)spiro[2.4]hepta-4,6-dien-5-yl]benzenesulfonamide;

4-[6-(2,3,5,6-tetrafluoro-4-trifluoromethylphenyl)spiro[2.4]hepta-4,6-dien-5-yl]benzenesulfonamide;

4-[6-(3,5-difluoro-4-methoxyphenyl)spiro[2.4]hepta-4,6-dien-5-yl]benzenesulfonamide;

4-[6-(3,5-dichloro-4-methoxyphenyl)spiro[2.4]hepta-4,6-dien-5-yl]benzenesulfonamide;

4-[6-(3,5-dibromo-4-methoxyphenyl)spiro[2.4]hepta-4,6-dien-5-yl]benzenesulfonamide;

4-[6-(2,3,4-trifluoro-4-methoxyphenyl)spiro[2.4]hepta-4,6-dien-5-yl]benzenesulfonamide;

4-[6-(2,3,4-trichloro-4-methoxyphenyl)spiro[2.4]hepta-4,6-dien-5-yl]benzenesulfonamide;

4-[6-(2,3,4-tribromo-4-methoxyphenyl)spiro[2.4]hepta-4,6-dien-5-yl]benzenesulfonamide;

4-[6-(2,4,5-trifluoro-4-methoxyphenyl)spiro[2.4]hepta-4,6-dien-5-yl]benzenesulfonamide;

4-[6-(2,4,5-trichloro-4-methoxyphenyl)spiro[2.4]hepta-4,6-dien-5-yl]benzenesulfonamide;

4-[6-(2,4,5-tribromo-4-methoxyphenyl)spiro[2.4]hepta-4,6-dien-5-yl]benzenesulfonamide;

4-[6-(3,4-dimethoxyphenyl)spiro[2.4]hepta-4,6-dien-5-yl]benzenesulfonamide;

4-[6-(3,4,5-trimethoxyphenyl)spiro[2.4]hepta-4,6-dien-5-yl]benzenesulfonamide;

4-[6-[3,4-bis(trifluoromethyl)phenyl]spiro[2.4]hepta-4,6-dien-5-yl]benzenesulfonamide;

4-[6-(3,4-dimethylphenyl)spiro[2.4]hepta-4,6-dien-5-yl]benzenesulfonamide;

4-[6-(3,4-difluorophenyl)spiro[2.4]hepta-4,6-dien-5-yl]benzenesulfonamide;

4-[6-(3,4-dichlorophenyl)spiro[2.4]hepta-4,6-dien-5-yl]benzenesulfonamide;

4-[6-(3,4-dibromophenyl)spiro[2.4]hepta-4,6-dien-5-yl]benzenesulfonamide;

4-[6-(3-chloro-4-fluorophenyl)spiro[2.4]hepta-4,6-dien-5-yl]benzenesulfonamide;

4-[6-(3-chloro-4-bromophenyl)spiro[2.4]hepta-4,6-dien-5-yl]benzenesulfonamide;

4-[6-(4-chloro-3-fluorophenyl)spiro[2.4]hepta-4,6-dien-5-yl]benzenesulfonamide;

4-[6-(4-chloro-3-bromophenyl)spiro[2.4]hepta-4,6-dien-5-yl]benzenesulfonamide;

4-[6-(3-methyl-4-fluorophenyl)spiro[2.4]hepta-4,6-dien-5-yl]benzenesulfonamide;

4-[6-(3-methyl-4-chlorophenyl)spiro[2.4]hepta-4,6-dien-5-yl]benzenesulfonamide;

4-[6-(3-methyl-4-bromophenyl)spiro[2.4]hepta-4,6-dien-5-yl]benzenesulfonamide;

4-[6-(3-methyl-4-trifluoromethylphenyl)spiro[2.4]hepta-4,6-dien-5-yl]benzenesulfonamide;
4-[6-(3-methyl-4-methoxyphenyl)spiro[2.4]hepta-4,6-dien-5-yl]benzenesulfonamide;
4-[6-(3-trifluoromethyl-4-fluorophenyl)spiro[2.4]hepta-4,6-dien-5-yl]benzenesulfonamide;
4-[6-(3-trifluoromethyl-4-chlorophenyl)spiro[2.4]hepta-4,6-dien-5-yl]benzenesulfonamide;
4-[6-(3-trifluoromethyl-4-bromophenyl)spiro[2.4]hepta-4,6-dien-5-yl]benzenesulfonamide;
4-[6-(3-trifluoromethyl-4-methylphenyl)spiro[2.4]hepta-4,6-dien-5-yl]benzenesulfonamide;
4-[6-(3-trifluoromethyl-4-methoxyphenyl)spiro[2.4]hepta-4,6-dien-5-yl]benzenesulfonamide;
4-[6-(3-fluoro-4-methoxyphenyl)spiro[2.4]hepta-4,6-dien-5-yl]benzenesulfonamide;
4-[6-(3-chloro-4-methoxyphenyl)spiro[2.4]hepta-4,6-dien-5-yl]benzenesulfonamide;
4-[6-(3-bromo-4-methoxyphenyl)spiro[2.4]hepta-4,6-dien-5-yl]benzenesulfonamide;
4-[6-(2,3,4,5,6-pentafluorophenyl)spiro[2.4]hepta-4,6-dien-5-yl]benzenesulfonamide;
4-[6-(4-methoxy-2,3,5,6-tetrafluorophenyl)spiro[2.4]hepta-4,6-dien-5-yl]benzenesulfonamide;
4-[6-(2,3,5,6-tetrafluoro-4-trifluoromethylphenyl)spiro[2.4]hepta-4,6-dien-5-yl]benzenesulfonamide;
4-[6-(3,5-difluoro-4-methoxyphenyl)spiro[2.4]hepta-4,6-dien-5-yl]benzenesulfonamide;
4-[6-(3,5-dichloro-4-methoxyphenyl)spiro[2.4]hepta-4,6-dien-5-yl]benzenesulfonamide;
4-[6-(3,5-dibromo-4-methoxyphenyl)spiro[2.4]hepta-4,6-dien-5-yl]benzenesulfonamide;
4-[6-(2,3,4-trifluoro-4-methoxyphenyl)spiro[2.4]hepta-4,6-dien-5-yl]benzenesulfonamide;
4-[6-(2,3,4-trichloro-4-methoxyphenyl)spiro[2.4]hepta-4,6-dien-5-yl]benzenesulfonamide;
4-[6-(2,3,4-tribromo-4-methoxyphenyl)spiro[2.4]hepta-4,6-dien-5-yl]benzenesulfonamide;
4-[6-(2,4,5-trifluoro-4-methoxyphenyl)spiro[2.4]hepta-4,6-dien-5-yl]benzenesulfonamide;
4-[6-(2,4,5-trichloro-4-methoxyphenyl)spiro[2.4]hepta-4,6-dien-5-yl]benzenesulfonamide;
4-[6-(2,4,5-tribromo-4-methoxyphenyl)spiro[2.4]hepta-4,6-dien-5-yl]benzenesulfonamide;
4-[6-(3,4-dimethoxyphenyl)spiro[2.4]hepta-4,6-dien-5-yl]benzenesulfonamide;
4-[6-(3,4,5-trimethoxyphenyl)spiro[2.4]hepta-4,6-dien-5-yl]benzenesulfonamide;
4-[6-[3,4-bis(trifluoromethyl)phenyl]spiro[2.4]hepta-4,6-dien-5-yl]benzenesulfonamide;
4-[6-(3,4-dimethylphenyl)spiro[2.4]hepta-4,6-dien-5-yl]benzenesulfonamide;
4-[6-(3,4-difluorophenyl)spiro[2.4]hepta-4,6-dien-5-yl]benzenesulfonamide;
4-[6-(3,4-dichlorophenyl)spiro[2.4]hepta-4,6-dien-5-yl]benzenesulfonamide;
4-[6-(3,4-dibromophenyl)spiro[2.4]hepta-4,6-dien-5-yl]benzenesulfonamide;
4-[6-(3-chloro-4-fluorophenyl)spiro[2.4]hepta-4,6-dien-5-yl]benzenesulfonamide;
4-[6-(3-chloro-4-bromophenyl)spiro[2.4]hepta-4,6-dien-5-yl]benzenesulfonamide;
4-[6-(4-chloro-3-fluorophenyl)spiro[2.4]hepta-4,6-dien-5-yl]benzenesulfonamide; and
4-[6-(4-chloro-3-bromophenyl)spiro[2.4]hepta-4,6-dien-5-yl]benzenesulfonamide.

Within Formula I there is a second subclass of compounds of high interest represented by Formula III:

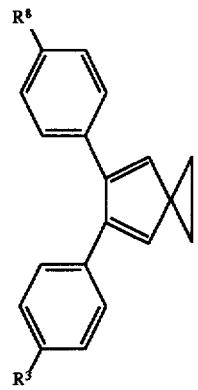

wherein $R^3$ is selected from alkylsulfonyl and sulfamyl; and wherein $R^8$ is selected from hydrido, halo, alkyl, alkoxy, alkylthio, cyano, haloalkyl, haloalkoxy, hydroxyalkyl, alkoxyalkyl, hydroxyl and mercapto; or a pharmaceutically-acceptable salt thereof.

A class of compounds of particular interest consists of those compounds of Formula III wherein $R^3$ is methylsulfonyl or sulfamyl; and wherein $R^8$ is selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl and ethoxymethyl; or a pharmaceutically-acceptable salt thereof.

A family of specific compounds of particular interest within Formula III consists of compounds and pharmaceutically-acceptable salts thereof as follows:
5-(4-fluorophenyl)-6-[4-(methylsulfonyl)phenyl]spiro[2.4]hepta-4,6-diene; and
4-[6-(4-fluorophenyl)spiro[2.4]hepta-4,6-dien-5-yl]benzenesulfonamide.

Within Formula I there is a third subclass of compounds of high interest represented by Formula IV:

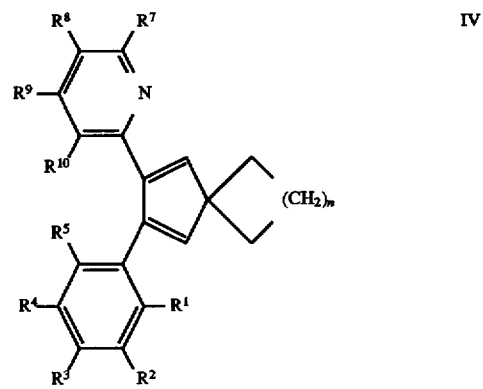

wherein n is a number selected from 0, 1, 2 and 3; and wherein each of $R^1$ through $R^5$ and $R^7$ through $R^{10}$ is independently selected from hydrido, halo, alkyl, alkoxy, alkylthio, cyano, haloalkyl, haloalkoxy, hydroxyalkyl, alkoxyalkyl, hydroxyl, mercapto, alkylsulfonyl, haloalkylsulfonyl and sulfamyl; or a pharmaceutically-acceptable salt thereof.

A preferred class of compounds consists of those compounds of Formula IV wherein n is a number selected from 0, 1 and 2; wherein each of $R^1$ through $R^5$ and $R^7$ through $R^{10}$ is independently selected from hydrido, halo, lower alkyl, lower alkoxy, lower alkylthio, cyano, lower haloalkyl, lower haloalkoxy, lower hydroxyalkyl, lower alkoxyalkyl, hydroxyl, mercapto, lower alkylsulfonyl, lower haloalkylsulfonyl and sulfamyl; or a pharmaceutically-acceptable salt thereof.

A class of compounds of particular interest consists of those compounds of Formula IV wherein each of $R^1$ through $R^5$ and $R^7$ through $R^{10}$ is independently selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl, ethoxymethyl, methylsulfonyl, fluoromethylsulfonyl, difluoromethylsulfonyl, trifluoromethylsulfonyl and sulfamyl; or a pharmaceutically-acceptable salt thereof.

A family of specific compounds of particular interest within Formula IV consists of compounds and pharmaceutically-acceptable salts thereof as follows:

2-[6-[4-(methylsulfonyl)phenyl]spiro[2.4]hepta-4,6-dien-5-yl]pyridine;

5-fluoro-2-[6-[4-(methylsulfonyl)phenyl]spiro [2.4]hepta-4,6-dien-5-yl]pyridine;

5-chloro-2-[6-[4-(methylsulfonyl)phenyl]spiro [2.4]hepta-4,6-dien-5-yl]pyridine;

5-methyl-2-[6-[4-(methylsulfonyl)phenyl]spiro [2.4]hepta-4,6-dien-5-yl]pyridine;

5-methoxy-2-[6-[4-(methylsulfonyl)phenyl]spiro [2.4]hepta-4,6-dien-5-yl]pyridine;

5-methylthio-2-[6-[4-(methylsulfonyl)phenyl]spiro [2.4]hepta-4,6-dien-5-yl]pyridine;

5-cyano-2-[6-[4-(methylsulfonyl)phenyl]spiro [2.4]hepta-4,6-dien-5-yl]pyridine;

5-trifluoromethyl-2-[6-[4-(methylsulfonyl) phenyl]spiro [2.4]hepta-4,6-dien-5-yl]pyridine;

4-[6-(pyridin-2-yl)spiro[2.4]hepta-4,6-dien-5-yl]benzenesulfonamide;

4-[6-(5-fluoropyridin-2-yl)spiro[2.4]hepta-4,6-dien-5-yl]benzenesulfonamide;

4-[6-(5-chloropyridin-2-yl)spiro[2.4]hepta-4,6-dien-5-yl]benzenesulfonamide;

4-[6-(5-methylpyridin-2-yl)spiro[2.4]hepta-4,6-dien-5-yl]benzenesulfonamide;

4-[6-(5-methoxypyridin-2-yl)spiro[2.4]hepta-4,6-dien-5-yl]benzenesulfonamide;

4-[6-(5-methylthiopyridin-2-yl)spiro[2.4]hepta-4,6-dien-5-yl]benzenesulfonamide;

4-[6-(5-cyanopyridin-2-yl)spiro[2.4]hepta-4,6-dien-5-yl]benzenesulfonamide;

4-[6-(5-trifluoromethylpyridin-2-yl)spiro[2.4]hepta-4,6-dien-5-yl]benzenesulfonamide;

2-[7-[4-(methylsulfonyl)phenyl]spiro[3.4]octa-5,7-dien-6-yl]pyridine;

5-fluoro-2-[7-[4-(methylsulfonyl) phenyl]spiro[3.4]octa-5,7-dien-6-yl]pyridine;

5-chloro-2-[7-[4-(methylsulfonyl)phenyl]spiro[3.4]octa-5,7-dien-6-yl]pyridine;

5-methyl-2-[7-[4-(methylsulfonyl)phenyl]spiro[3.4]octa-5,7-dien-6-yl]pyridine;

5-methoxy-2-[7-[4-(methylsulfonyl)phenyl]spiro[3.4]octa-5,7-dien-6-yl]pyridine;

5-methylthio-2-[7-[4-(methylsulfonyl)phenyl]spiro[3.4]octa-5,7-dien-6-yl]pyridine;

5-cyano-2-[7-[4-(methylsulfonyl)phenyl]spiro[3.4]octa-5,7-dien-6-yl]pyridine;

5-trifluoromethyl-2-[7-[4-(methylsulfonyl)phenyl]spiro[3.4]octa-5,7-dien-6-yl]pyridine;

4-[7-(pyridin-2-yl)spiro[3.4]octa-5,7-dien-6-yl]benzenesulfonamide;

4-[7-(5-fluoropyridin-2-yl)spiro[3.4]octa-5,7-dien-6-yl]benzenesulfonamide;

4-[7-(5-chloropyridin-2-yl)spiro[3.4]octa-5,7-dien-6-yl]benzenesulfonamide;

4-[7-(5-methylpyridin-2-yl)spiro[3.4]octa-5,7-dien-6-yl]benzenesulfonamide;

4-[7-(5-methoxypyridin-2-yl)spiro[3.4]octa-5,7-dien-6-yl]benzenesulfonamide;

4-[7-(5-methylthiopyridin-2-yl)spiro[3.4]octa-5,7-dien-6-yl]benzenesulfonamide;

4-[7-(5-cyanopyridin-2-yl)spiro[3.4]octa-5,7-dien-6-yl]benzenesulfonamide;

4-[7-(5-trifluoromethylpyridin-2-yl)spiro[3.4]octa-5,7-dien-6-yl]benzenesulfonamide;

2-[3-[4-(methylsulfonyl)phenyl]spiro[4.4]nona-1,3-dien-2-yl]pyridine;

5-fluoro-2-[3-[4-(methylsulfonyl)phenyl]spiro[4.4]nona-1,3-dien-2-yl]pyridine;

5-chloro-2-[3-[4-(methylsulfonyl)phenyl]spiro[4.4]nona-1,3-dien-2-yl]pyridine;

5-methyl-2-[3-[4-(methylsulfonyl)phenyl]spiro[4.4]nona-1,3-dien-2-yl]pyridine;

5-methoxy-2-[3-[4-(methylsulfonyl)phenyl]spiro[4.4]nona-1,3-dien-2-yl]pyridine;

5-methylthio-2-[3-[4-(methylsulfonyl)phenyl]spiro[4.4]nona-1,3-dien-2-yl]pyridine;

5-cyano-2-[3-[4-(methylsulfonyl)phenyl]spiro[4.4]nona-1,3-dien-2-yl]pyridine;

5-trifluoromethyl-2-[3-[4-(methylsulfonyl)phenyl]spiro[4.4]nona-1,3-dien-2-yl]pyridine;

4-[3-(pyridin-2-yl)spiro[4.4]nona-1,3-dien-2-yl]benzenesulfonamide;

4-[3-(5-fluoropyridin-2-yl)spiro[4.4]nona-1,3-dien-2-yl]benzenesulfonamide;

4-[3-(5-chloropyridin-2-yl)spiro[4.4]nona-1,3-dien-2-yl]benzenesulfonamide;

4-[3-(5-methylpyridin-2-yl)spiro[4.4]nona-1,3-dien-2-yl]benzenesulfonamide;

4-[3-(5-methoxypyridin-2-yl)spiro[4.4]nona-1,3-dien-2-yl]benzenesulfonamide;

4-[3-(5-methylthiopyridin-2-yl)spiro[4.4]nona-1,3-dien-2-yl]benzenesulfonamide;

4-[3-(5-cyanopyridin-2-yl)spiro[4.4]nona-1,3-dien-2-yl]benzenesulfonamide;

4-[3-(5-trifluoromethylpyridin-2-yl)spiro[4.4]nona-1,3-dien-2-yl]benzenesulfonamide;

2-(6-phenylspiro[2.4]hepta-4,6-dien-5-yl)-5-(methylsulfonyl)pyridine;

2-[6-(4-fluorophenyl)spiro[2.4]hepta-4,6-dien-5-yl]-5-(methylsulfonyl)pyridine;

2-[6-(4-chlorophenyl)spiro[2.4]hepta-4,6-dien-5-yl]-5-(methylsulfonyl)pyridine;

2-[6-(4-methylphenyl)spiro[2.4]hepta-4,6-dien-5-yl]-5-(methylsulfonyl)pyridine;

2-[6-(4-methoxyphenyl)spiro[2.4]hepta-4,6-dien-5-yl]-5-(methylsulfonyl)pyridine;

2-[6-(4-methylthiophenyl)spiro[2.4]hepta-4,6-dien-5-yl]-5-(methylsulfonyl) pyridine;

2-[6-(4-cyanophenyl)spiro[2.4]hepta-4,6-dien-5-yl]-5-(methylsulfonyl)pyridine;

2-[6-(4-trifluoromethylphenyl)spiro[2.4]hepta-4,6-dien-5-yl]-5-(methylsulfonyl) pyridine;

2-(6-phenylspiro[2.4]hepta-4,6-dien-5-yl]-5-pyridinesulfonamide;

2-[6-(4-fluorophenyl)spiro[2.4]hepta-4,6-dien-5-yl]-5-pyridinesulfonamide;

2-[6-(4-chlorophenyl)spiro[2.4]hepta-4,6-dien-5-yl]-5-pyridinesulfonamide;

2-[6-(4-methylphenyl)spiro[2.4]hepta-4,6-dien-5-yl]-5-pyridinesulfonamide;

2-[6-(4-methoxyphenyl)spiro[2.4]hepta-4,6-dien-5-yl]-5-pyridinesulfonamide;

2-[6-(4-methylthiophenyl)spiro[2.4]hepta-4,6-dien-5-yl]-5-pyridinesulfonamide;

2-[6-(4-cyanophenyl)spiro[2.4]hepta-4,6-dien-5-yl]-5-pyridinesulfonamide;

2-[6-(4-trifluoromethylphenyl)spiro[2.4]hepta-4,6-dien-5-yl]-5-pyridinesulfonamide;

2-(7-phenyl spiro[3.4]octa-5,7-dien-6-yl)-5-(methylsulfonyl)pyridine;

2-[7-(4-fluorophenyl)spiro[3.4]octa-5,7-dien-6-yl]-5-(methylsulfonyl)pyridine;

2-[7-(4-chlorophenyl)spiro[3.4]octa-5,7-dien-6-yl]-5-(methylsulfonyl)pyridine;

2-[7-(4-methylphenyl)spiro[3.4]octa-5,7-dien-6-yl]-5-(methylsulfonyl)pyridine;

2-[7-(4-methoxyphenyl)spiro[3.4]octa-5,7-dien-6-yl]-5-(methylsulfonyl)pyridine;

2-[7-(4-methylthiophenyl)spiro[3.4]octa-5,7-dien-6-yl]-5-(methylsulfonyl)pyridine;

2-[7-(4-cyanophenyl)spiro[3.4]octa-5,7-dien-6-yl]-5-(methylsulfonyl)pyridine;

2-[7-(4-trifluoromethylphenyl)spiro[3.4]octa-5,7-dien-6-yl]-5-(methylsulfonyl)pyridine;

2-(7-phenyl spiro[3.4]octa-5,7-dien-6-yl)-5-pyridinesulfonamide;

2-[7-(4-fluorophenyl)spiro[3.4]octa-5,7-dien-6-yl]-5-pyridinesulfonamide;

2-[7-(4-chlorophenyl)spiro[3.4]octa-5,7-dien-6-yl]-5-pyridinesulfonamide;

2-[7-(4-methylphenyl)spiro[3.4]octa-5,7-dien-6-yl]-5-pyridinesulfonamide;

2-[7-(4-methoxyphenyl)spiro[3.4]octa-5,7-dien-6-yl]-5-pyridinesulfonamide;

2-[7-(4-methylthiophenyl)spiro[3.4]octa-5,7-dien-6-yl]-5-pyridinesulfonamide;

2-[7-(4-cyanophenyl)spiro[3.4]octa-5,7-dien-6-yl]-5-pyridinesulfonamide;

2-[7-(4-trifluoromethylphenyl)spiro[3.4]octa-5,7-dien-6-yl]-5-pyridinesulfonamide;

2-(3-phenylspiro[4.4]nona-1,3-dien-2-yl)-5-(methylsulfonyl)pyridine;

2-[3-(4-fluorophenyl)spiro[4.4]nona-1,3-dien-2-yl]-5-(methylsulfonyl)pyridine;

2-[3-(4-chlorophenyl)spiro[4.4]nona-1,3-dien-2-yl]-5-(methylsulfonyl)pyridine;

2-[3-(4-methylphenyl)spiro[4.4]nona-1,3-dien-2-yl]-5-(methylsulfonyl)pyridine;

2-[3-(4-methoxyphenyl)spiro[4.4]nona-1,3-dien-2-yl]-5-(methylsulfonyl)pyridine;

2-[3-(4-methylthiophenyl)spiro[4.4]nona-1,3-dien-2-yl]-5-(methylsulfonyl)pyridine;

2-[3-(4-cyanophenyl)spiro[4.4]nona-1,3-dien-2-yl]-5-(methylsulfonyl)pyridine;

2-[3-(4-trifluoromethylphenyl)spiro[4.4]nona-1,3-dien-2-yl]-5-(methylsulfonyl)pyridine;

2-(3-phenylspiro[4.4]nona-1,3-dien-2-yl)-5-pyridinesulfonamide;

2-[3-(4-fluorophenyl)spiro[4.4]nona-1,3-dien-2-yl]-5-pyridinesulfonamide;

2-[3-(4-chlorophenyl)spiro[4.4]nona-1,3-dien-2-yl]-5-pyridinesulfonamide;

2-[3-(4-methylphenyl)spiro[4.4]nona-1,3-dien-2-yl]-5-pyridinesulfonamide;

2-[3-(4-methoxyphenyl)spiro[4.4]nona-1,3-dien-2-yl]-5-pyridinesulfonamide;

2-[3-(4-cyanophenyl)spiro[4.4]nona-1,3-dien-2-yl]-5-pyridinesulfonamide; and

2-[3-(4-trifluoromethylphenyl)spiro[4.4]nona-1,3-dien-2-yl]-5-pyridinesulfonamide.

Within Formula I there is a fourth subclass of compounds of high interest represented by Formula V:

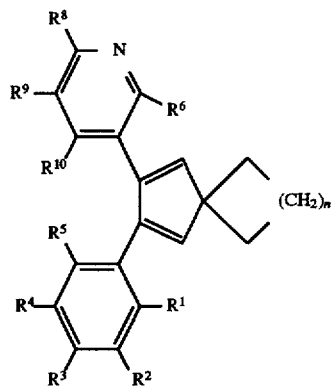

wherein n is a number selected from 0, 1, 2 and 3; and wherein each of $R^1$ through $R^6$ and $R^8$ through $R^{10}$ is independently selected from hydrido, halo, alkyl, alkoxy, alkylthio, cyano, haloalkyl, haloalkoxy, hydroxyalkyl, alkoxyalkyl, hydroxyl, mercapto, alkylsulfonyl, haloalkylsulfonyl and sulfamyl; or a pharmaceutically-acceptable salt thereof.

A preferred class of compounds consists of those compounds of Formula V wherein n is a number selected from 0, 1 and 2; wherein each of $R^1$ through $R^6$ and $R^8$ through $R^{10}$ is independently selected from hydrido, halo, lower alkyl, lower alkoxy, lower alkylthio, cyano, lower haloalkyl, lower haloalkoxy, lower hydroxyalkyl, lower alkoxyalkyl, hydroxyl, mercapto, lower alkylsulfonyl, lower haloalkylsulfonyl and sulfamyl; or a pharmaceutically-acceptable salt thereof.

A class of compounds of particular interest consists of those compounds of Formula V wherein each of $R^1$ through $R^6$ and $R^8$ through $R^{10}$ is independently selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, trifluoromethoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, methoxymethyl, ethoxymethyl, methylsulfonyl, fluoromethylsulfonyl, difluoromethylsulfonyl, trifluoromethylsulfonyl and sulfamyl; or a pharmaceutically-acceptable salt thereof.

A family of specific compounds of particular interest within Formula V consists of compounds and pharmaceutically-acceptable salts thereof as follows:

5-[6-[4-(methylsulfonyl)phenyl]spiro[2.4]hepta-4,6-dien5-yl]pyridine;

2-fluoro-5-[6-[4-(methylsulfonyl)phenyl]spiro[2.4]hepta-4,6-dien-5-yl]pyridine;

2-chloro-5-[6-[4-(methylsulfonyl)phenyl]spiro[2.4]hepta-4,6-dien-5-yl]pyridine;
2-methyl-5-[6-[4-(methylsulfonyl)phenyl]spiro[2.4]hepta-4,6-dien-5-yl]pyridine;
2-methoxy-5-[6-[4-(methylsulfonyl)phenyl]spiro[2.4]hepta-4,6-dien-5-yl]pyridine;
2-methylthio-5-[6-[4-(methylsulfonyl)phenyl]spiro[2.4]hepta-4,6-dien-5-yl]pyridine;
2-cyano-5-[6-[4-(methylsulfonyl)phenyl]spiro[2.4]hepta-4,6-dien-5-yl]pyridine;
2-trifluoromethyl-5-[6-[4-(methylsulfonyl)phenyl]spiro[2.4]hepta-4,6-dien-5-yl]pyridine;
4-[6-(pyridin-5-yl)spiro[2.4]hepta-4,6-dien-5-yl]benzenesulfonamide;
4-[6-(2-fluoropyridin-5-yl)spiro[2.4]hepta-4,6-dien-5-yl]benzenesulfonamide;
4-[6-(2-chloropyridin-5-yl)spiro[2.4]hepta-4,6-dien-5-yl]benzenesulfonamide;
4-[6-(2-methylpyridin-5-yl)spiro[2.4]hepta-4,6-dien-5-yl]benzenesulfonamide;
4-[6-(2-methoxypyridin-5-yl)spiro[2.4]hepta-4,6-dien-5-yl]benzenesulfonamide;
4-[6-(2-methylthiopyridin-5-yl)spiro[2.4]hepta-4,6-dien-5-yl]benzenesulfonamide;
4-[6-(2-cyanopyridin-5-yl)spiro[2.4]hepta-4,6-dien-5-yl]benzenesulfonamide;
4-[6-(2-trifluoromethylpyridin-5-yl)spiro[2.4]hepta-4,6-dien-5-yl]benzenesulfonamide;
5-[7-[4-(methylsulfonyl)phenyl]spiro[3.4]octa-5,7-dien-6-yl]pyridine;
2-fluoro-5-[7-[4-(methylsulfonyl)phenyl]spiro[3.4]octa-5,7-dien-6-yl]pyridine;
2-chloro-5-[7-[4-(methylsulfonyl)phenyl]spiro[3.4]octa-5,7-dien-6-yl]pyridine;
2-methyl-5-[7-[4-(methylsulfonyl)phenyl]spiro[3.4]octa-5,7-dien-6-yl]pyridine;
2-methoxy-5-[7-[4-(methylsulfonyl)phenyl]spiro[3.4]octa-5,7-dien-6-yl]pyridine;
2-methylthio-5-[7-[4-(methylsulfonyl)phenyl]spiro[3.4]octa-5,7-dien-6-yl]pyridine;
2-cyano-5-[7-[4-(methylsulfonyl)phenyl]spiro[3.4]octa-5,7-dien-6-yl]pyridine;
2-trifluoromethyl-5-[7-[4-(methylsulfonyl)phenyl]spiro[3.4]octa-5,7-dien-6-yl]pyridine;
4-[7-(pyridin-5-yl)spiro[3.4]octa-5,7-dien-6-yl]benzenesulfonamide;
4-[7-(2-fluoropyridin-5-yl)spiro[3.4]octa-5,7-dien-6-yl]benzenesulfonamide;
4-[7-(2-chloropyridin-5-yl)spiro[3.4]octa-5,7-dien-6-yl]benzenesulfonamide;
4-[7-(2-methylpyridin-5-yl)spiro[3.4]octa-5,7-dien-6-yl]benzenesulfonamide;
4-[7-(2-methoxypyridin-5-yl)spiro[3.4]octa-5,7-dien-6-yl]benzenesulfonamide;
4-[7-(2-methylthiopyridin-5-yl)spiro[3.4]octa-5,7-dien-6-yl]benzenesulfonamide;
4-[7-(2-cyanopyridin-5-yl)spiro[3.4]octa-5,7-dien-6-yl]benzenesulfonamide;
4-[7-(2-trifluoromethylpyridin-5-yl)spiro[3.4]octa-5,7-dien-6-yl]benzenesulfonamide;
5-[3-[4-(methylsulfonyl)phenyl]spiro[4.4]nona-1,3-dien-2-yl]pyridine;
2-fluoro-5-[3-[4-(methylsulfonyl)phenyl]spiro[4.4]nona-1,3-dien-2-yl]pyridine;
2-chloro-5-[3-[4-(methylsulfonyl)phenyl]spiro[4.4]nona-1,3-dien-2-yl]pyridine;
2-methyl-5-[3-[4-(methylsulfonyl)phenyl]spiro[4.4]nona-1,3-dien-2-yl]pyridine;
2-methoxy-5-[3-[4-(methylsulfonyl)phenyl]spiro[4.4]nona-1,3-dien-2-yl]pyridine;
2-methylthio-5-[3-[4-(methylsulfonyl)phenyl]spiro[4.4]nona-1,3-dien-2-yl]pyridine;
2-trifluoromethyl-5-[3-[4-(methylsulfonyl)phenyl]spiro[4.4]nona-1,3-dien-2-yl]pyridine;
4-[3-(pyridin-5-yl)spiro[4.4]nona-1,3-dien-2-yl]benzenesulfonamide;
4-[3-(2-fluoropyridin-5-yl)spiro[4.4]nona-1,3-dien-2-yl]benzenesulfonamide;
4-[3-(2-chloropyridin-5-yl)spiro[4.4]nona-1,3-dien-2-yl]benzenesulfonamide;
4-[3-(2-methylpyridin-5-yl)spiro[4.4]nona-1,3-dien-2-yl]benzenesulfonamide;
4-[3-(2-methoxypyridin-5-yl)spiro[4.4]nona-1,3-dien-2-yl]benzenesulfonamide;
4-[3-(2-methylthiopyridin-5-yl)spiro[4.4]nona-1,3-dien-2-yl]benzenesulfonamide;
4-[3-(2-cyanopyridin-5-yl)spiro[4.4]nona-1,3-dien-2-yl]benzenesulfonamide;
4-[3-(2-trifluoromethylpyridin-5-yl)spiro[4.4]nona-1,3-dien-2-yl]benzenesulfonamide;
5-(6-phenylspiro[2.4]hepta-4,6-dien-5-yl)-2-(methylsulfonyl)pyridine;
5-[6-(4-fluorophenyl)spiro[2.4]hepta-4,6-dien-5-yl]-2-(methylsulfonyl)pyridine;
5-[6-(4-chlorophenyl)spiro[2.4]hepta-4,6-dien-5-yl]-2-(methylsulfonyl)pyridine;
5-[6-(4-methylphenyl)spiro[2.4]hepta-4,6-dien-5-yl]-2-(methylsulfonyl)pyridine;
5-[6-(4-methoxyphenyl)spiro[2.4]hepta-4,6-dien-5-yl]-2-(methylsulfonyl)pyridine;
5-[6-(4-methylthiophenyl)spiro[2.4]hepta-4,6-dien-5-yl]2-(methylsulfonyl)pyridine;
5-[6-(4-cyanophenyl)spiro[2.4]hepta-4,6-dien-5-yl]-2-(methylsulfonyl)pyridine;
5-[6-(4-trifluoromethylphenyl)spiro[2.4]hepta-4,6-dien-5-yl]-2-(methylsulfonyl)pyridine;
5-(6-phenylspiro[2.4]hepta-4,6-dien-5-yl)-2-pyridinesulfonamide;
5-[6-(4-fluorophenyl)spiro[2.4]hepta-4,6-dien-5-yl]-2-pyridinesulfonamide;
5-[6-(4-chlorophenyl)spiro[2.4]hepta-4,6-dien-5-yl]-2-pyridinesulfonamide;
5-[6-(4-methylphenyl)spiro[2.4]hepta-4,6-dien-5-yl]-2-pyridinesulfonamide;
5-[6-(4-methoxyphenyl)spiro[2.4]hepta-4,6-dien-5-yl]-2-pyridinesulfonamide;
5-[6-(4-methylthiophenyl)spiro[2.4]hepta-4,6-dien-5-yl]-2-pyridinesulfonamide;
5-[6-(4-cyanophenyl)spiro[2.4]hepta-4,6-dien-5-yl]-2-pyridinesulfonamide;
5-[6-(4-trifluoromethylphenyl)spiro[2.4]hepta-4,6-dien-5-yl]-2-pyridinesulfonamide;
5-(7-phenylspiro[3.4]octa-5,7-dien-6-yl)-2-(methylsulfonyl)pyridine;
5-[7-(4-fluorophenyl)spiro[3.4]octa-5,7-dien-6-yl]-2-(methylsulfonyl)pyridine;
5-[7-(4-chlorophenyl)spiro[3.4]octa-5,7-dien-6-yl]-2-(methylsulfonyl)pyridine;
5-[7-(4-methylphenyl)spiro[3.4]octa-5,7-dien-6-yl]-2-(methylsulfonyl)pyridine;
5-[7-(4-methoxyphenyl)spiro[3.4]octa-5,7-dien-6-yl]-2-(methylsulfonyl)pyridine;
5-[7-(4-methylthiophenyl)spiro[3.4]octa-5,7-dien-6-yl]-2-(methylsulfonyl)pyridine;
5-[7-(4-cyanophenyl)spiro[3.4]octa-5,7-dien-6-yl]-2-(methylsulfonyl)pyridine;
5-[7-(4-trifluoromethylphenyl)spiro[3.4]octa-5,7-dien-6-yl]-2-(methylsulfonyl)pyridine;
5-(7-phenylspiro[3.4]octa-5,7-dien-6-yl)-2-pyridinesulfonamide;
5-[7-(4-fluorophenyl)spiro[3.4]octa-5,7-dien-6-yl]-2-pyridinesulfonamide;
5-[7-(4-chlorophenyl)spiro[3.4]octa-5,7-dien-6-yl]-2-pyridinesulfonamide;

5-[7-(4-methylphenyl)spiro[3.4]octa-5,7-dien-6-yl]-2-pyridinesulfonamide;

5-[7-(4-methoxyphenyl)spiro[3.4]octa-5,7-dien-6-yl]-2-pyridinesulfonamide;

5-[7-(4-cyanophenyl)spiro[3.4]octa-5,7-dien-6-yl]-2-pyridinesulfonamide;

5-[7-(4-trifluoromethylphenyl)spiro[3.4]octa-5,7-dien-6-yl]-2-pyridinesulfonamide;

5-(3-phenylspiro[4.4]nona-1,3-dien-2-yl)-2-(methylsulfonyl)pyridine;

5-[3-4-fluorophenyl)spiro[4.4]nona-1,3-dien-2-yl]-2-methylsulfonyl)pyridine;

5-[3-4-chlorophenyl)spiro[4.4]nona-1,3-dien-2-yl]-2-methylsulfonyl)pyridine;

5-[3-4-methylphenyl)spiro[4.4]nona-1,3-dien-2-yl]-2-methylsulfonyl)pyridine;

5-[3-4-methoxyphenyl)spiro[4.4]nona-1,3-dien-2-yl]-2-(methylsulfonyl)pyridine;

5-[3-(4-methylthiophenyl)spiro[4.4]nona-1,3-dien-2-yl]-2-(methylsulfonyl)pyridine;

5-[3-(4-cyanophenyl)spiro[4.4]nona-1,3-dien-2-yl]-2-(methylsulfonyl)pyridine;

5-[3-(4-trifluoromethylphenyl)spiro[4.4]nona-1,3-dien-2-yl]-2-(methylsulfonyl)pyridine;

5-(3-phenylspiro[4.4]nona-1,3-dien-2-yl)-2-pyridinesulfonamide;

5-[3-(4-fluorophenyl)spiro[4.4]nona-1,3-dien-2-yl]-2-pyridinesulfonamide;

5-[3-(4-chlorophenyl)spiro[4.4]nona-1,3-dien-2-yl]-2-pyridinesulfonamide;

5-[3-(4-methylphenyl)spiro[4.4]nona-1,3-dien-2-yl]-2-pyridinesulfonamide;

5-[3-(4-methoxyphenyl)spiro[4.4]nona-1,3-dien-2-yl]-2-pyridinesulfonamide;

5-[3-(4-methylthiophenyl)spiro[4.4]nona-1,3-dien-2-yl]-2-pyridinesulfonamide;

5-[3-(4-cyanophenyl)spiro[4.4]nona-1,3-dien-2-yl]-2-pyridinesulfonamide; and

5-[3-(4-trifluoromethylphenyl)spiro[4.4]nona-1,3-dien-2-yl]-2-pyridinesulfonamide.

Within Formula I there is a fifth subclass of compounds of high interest represented by Formula VI:

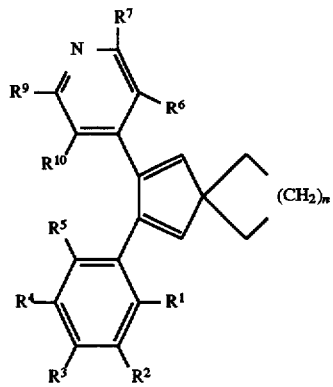

VI wherein n is a number selected from 0, 1, 2 and 3; and wherein each of $R^1$ through $R^7$, $R^9$ and $R^{10}$ is independently selected from hydrido, halo, alkyl, alkoxy, alkylthio, cyano, haloalkyl, haloalkoxy, hydroxyalkyl, alkoxyalkyl, hydroxyl, mercapto, alkylsulfonyl, haloalkylsulfonyl and sulfamyl; or a pharmaceutically-acceptable salt thereof.

A preferred class of compounds consists of those compounds of Formula VI wherein n is a number selected from 0, 1 and 2; wherein each of $R^1$ through $R^7$, $R^9$ and $R^{10}$ is independently selected from hydrido, halo, lower alkyl, lower alkylthio, cyano, hydroxyl, mercapto, lower haloalkyl, lower haloalkoxy, lower alkoxy, lower hydroxyalkyl, lower alkoxyalkyl, lower alkylsulfonyl, lower haloalkylsulfonyl and sulfamyl; or a pharmaceutically-acceptable salt thereof.

A class of compounds of particular interest consists of those compounds of Formula VI wherein each of $R^1$ through $R^7$, $R^9$ and $R^{10}$ is independently selected from hydrido, fluoro, chloro, bromo, iodo, methyl, ethyl, n-propyl, isopropyl, butyl, tert-butyl, isobutyl, methoxy, ethoxy, propoxy, butoxy, methylthio, ethylthio, cyano, hydroxyl, mercapto, trifluoromethoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, methoxymethyl, ethoxymethyl, methylsulfonyl, fluoromethylsulfonyl, difluoromethylsulfonyl, trifluoromethylsulfonyl and sulfamyl; or a pharmaceutically-acceptable salt thereof.

A family of specific compounds of particular interest within Formula VI consists of compounds and pharmaceutically-acceptable salts thereof as follows:

4-[6-[4-(methylsulfonyl)phenyl]spiro[2.4]hepta-4,6-dien-5-yl]pyridine;

4-[6-(4-pyridinyl)spiro[2.4]hepta-4,6-dien-5-yl]benzenesulfonamide;

4-[7-[4-(methylsulfonyl)phenyl]spiro[3.4]octa-5,7-dien-6-yl]pyridine;

4-[7-(4-pyridinyl)spiro[3.4]octa-5,7-dien-6-yl]benzenesulfonamide;

4-[3-[4-(methylsulfonyl)phenyl]spiro[4.4]nona-1,3-dien-2-yl]pyridine; and

4-[3-(4-pyridinyl)spiro[4.4]nona-1,3-dien-2-yl]benzenesulfonamide.

Where the term "alkyl" is used, either alone or within other terms such as "haloalkyl", "alkylsulfonyl", "alkoxyalkyl" and "hydroxyalkyl", embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. The term "hydroxyalkyl" embraces linear or branched alkyl radicals having one to about twelve carbon atoms any one of which may be substituted with one or more hydroxyl radicals. The terms "alkoxy" and "alkoxyalkyl" embrace linear or branched oxy-containing radicals each having alkyl portions of one to about twelve carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. The "alkoxy"

or "alkoxyalkyl" radicals may be further substituted with one or more halo atoms, such as fluoro, chloro or bromo, to provide haloalkoxy or haloalkoxyalkyl radicals. The term "alkylthio" embraces radicals containing a linear or branched alkyl radical, of one to about twelve carbon atoms attached to a divalent sulfur atom, such as a methythio radical, ($CH_3$—S—). The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. The "alkylsulfonyl" radicals may be further substituted with one or more halo atoms, such as fluoro, chloro or bromo, to provide haloalkylsulfonyl radicals. The terms "sulfamyl" or "sulfonamidyl" denotes a sulfonyl radical substituted with an amine radical, forming a sulfonamide (—$SO_2NH_2$).

The present invention comprises a pharmaceutical composition comprising a therapeutically effective amount of a compound of Formula I in association with at least one pharmaceutically-acceptable carrier, adjuvant or diluent.

The present invention also comprises a method of treating inflammation or inflammation-associated disorders in a subject, the method comprising administering to the subject having such inflammation or disorder a therapeutically-effective amount of a compound of Formula I.

Also included in the family of compounds of Formula I are isomeric forms including diastereoisomers, prodrugs and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I. The term "prodrug" embraces compounds which are metabolized in vivo into compounds of the invention.

GENERAL SYNTHETIC PROCEDURES

The compounds of the invention can be synthesized according to the following procedures of Schemes I–XX, wherein the $R^1$–$R^{10}$ substituents are as defined for Formula I, above, except where further noted.

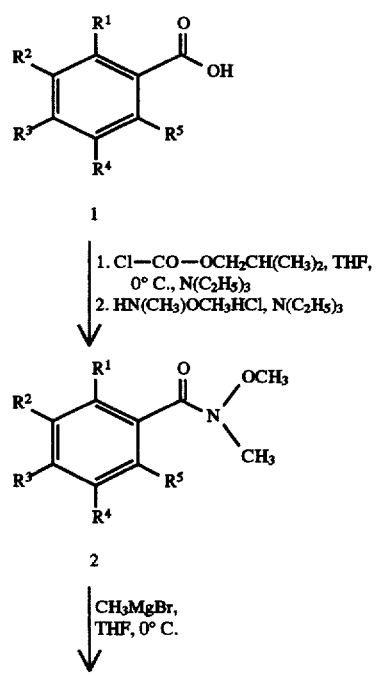

-continued
Scheme I

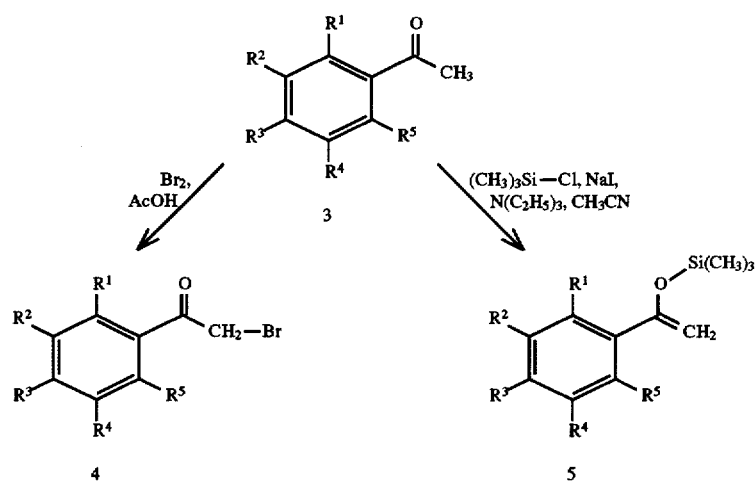

Synthetic Scheme I shows the three step procedure used to prepare the bromoacetophenones 4 and the phenyl silyl enol ethers 5 from commercially available benzoic acids 1. In step one, a THF solution at 0° C. of the benzoic acids 1 and two equivalents of triethylamine are sequentially treated with isobutyl chloroformate and N-hydroxymethyl-N-methylamine hydrochloride to give the Weinreb amides 2 [see: S. Nahm and S. M. Weinreb, *Tetrahedron Lett.*, 21, 3815 (1981)]. In step two, the amides 2 are reacted with methylmagnesium bromide to give the corresponding acetophenones 3. In step three, the acetophenones 3 are either treated with bromine in acetic acid to give the corresponding bromoacetophenones 4 or chlorotrimethylsilane in acetonitrile in the presence of triethylamine and sodium iodide to give the corresponding phenyl silyl enol ethers 5.

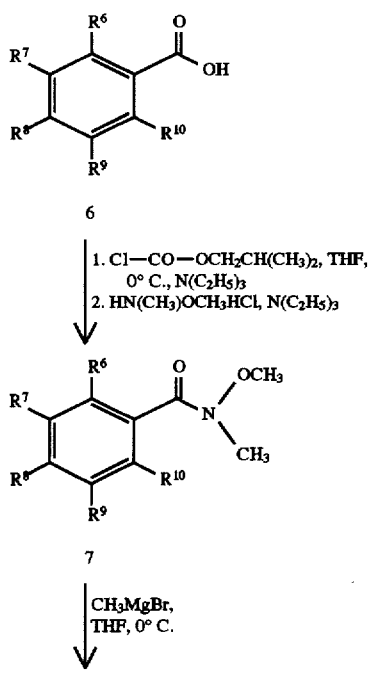

Scheme II -continued

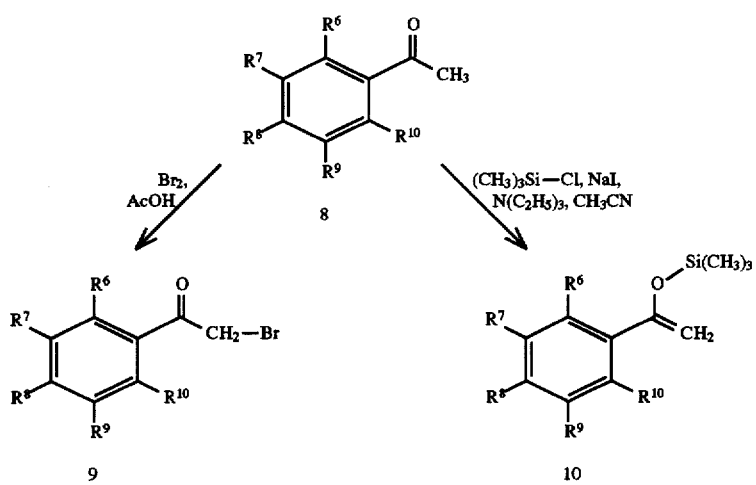

Synthetic Scheme II shows the three step procedure used to prepare the bromoacetophenones 9 and the phenyl silyl enol ethers 10 from commercially available benzoic acids 6. In step one, a THF solution at 0° C. of the benzoic acids 6 and two equivalents of triethylamine are sequentially treated with isobutyl chloroformate and N-hydroxymethyl-N-methylamine hydrochloride to give the Weinreb amides 7. In step two, the amides 7 are reacted with methylmagnesium bromide to give the corresponding acetophenones 8. In step three, the acetophenones 8 are either treated with bromine in acetic acid to give the corresponding bromoacetophenones 9 or chlorotrimethylsilane in acetonitrile in the presence of triethylamine and sodium iodide to give the corresponding phenyl silyl enol ethers 10.

Scheme III

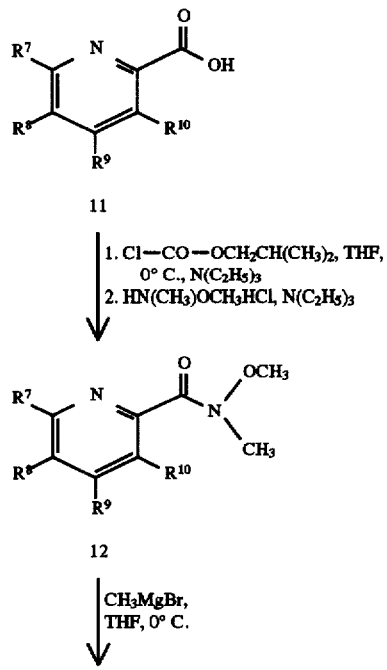

-continued
Scheme III

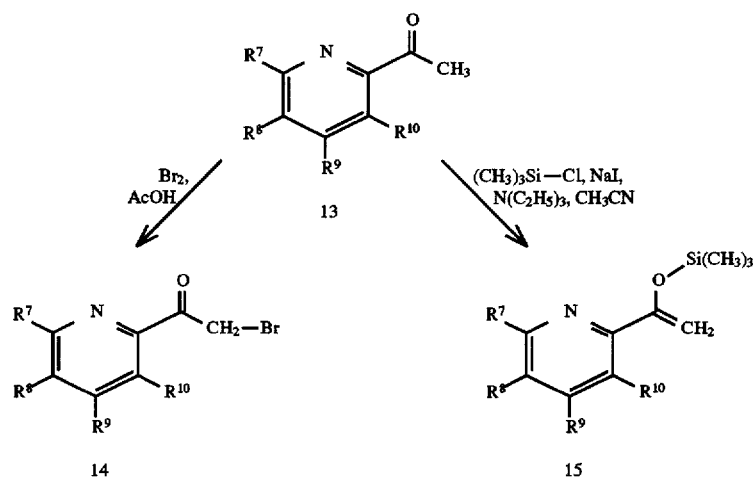

Synthetic Scheme III shows the three step procedure used to prepare the 2-(bromoacetyl)pyridines 14 and the 2-pyridinyl silyl enol ethers 15 from commercially available picolinic acids 11. In step one, a THF solution at 0° C. of the picolinic acids 11 and two equivalents of triethylamine are sequentially treated with isobutyl chloroformate and N-hydroxymethyl-N-methylamine hydrochloride to give the Weinreb amides 12. In step two, the amides 12 are reacted with methylmagnesium bromide to give the corresponding 2-acetylpyridines 13. In step three, the 2-acetylpyridines 13 are either treated with bromine in acetic acid to give the corresponding 2-(bromoacetyl)pyridines 14 or chlorotrimethylsilane in acetonitrile in the presence of triethylamine and sodium iodide to give the corresponding 2-pyridinyl silyl enol ethers 15.

Scheme IV

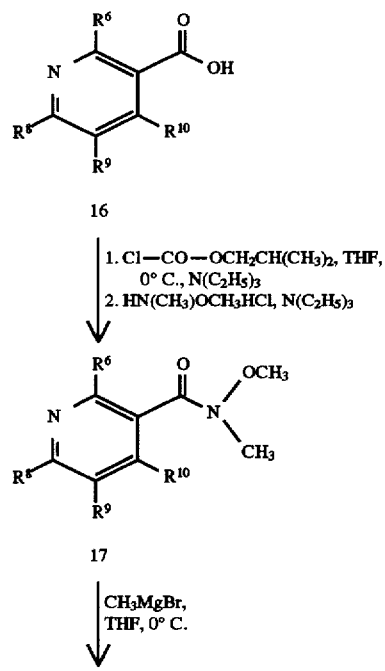

-continued
Scheme IV

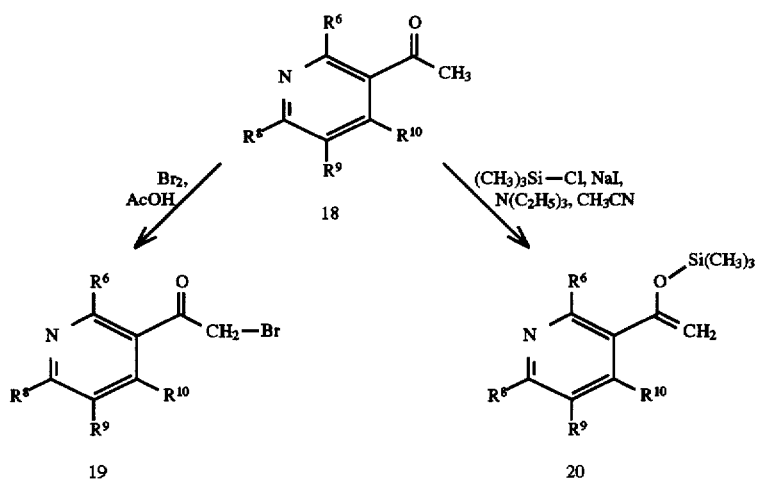

Synthetic Scheme IV shows the three step procedure used to prepare the 3-(bromoacetyl)pyridines 19 and the 3-pyridinyl silyl enol ethers 20 from commercially available nicotinic acids 16. In step one, a THF solution at 0° C. of the nicotinic acids 16 and two equivalents of triethylamine are sequentially treated with isobutyl chloroformate and N-hydroxymethyl-N-methylamine hydrochloride to give the Weinreb amides 17. In step two, the amides 17 are reacted with methylmagnesium bromide to give the corresponding 3-acetylpyridines 18. In step three, the 3-acetylpyridines 18 are either treated with bromine in acetic acid to give the corresponding 3-(bromoacetyl)pyridines 19 or chlorotrimethylsilane in acetonitrile in the presence of triethylamine and sodium iodide to give the corresponding 3-pyridinyl silyl enol ethers 20.

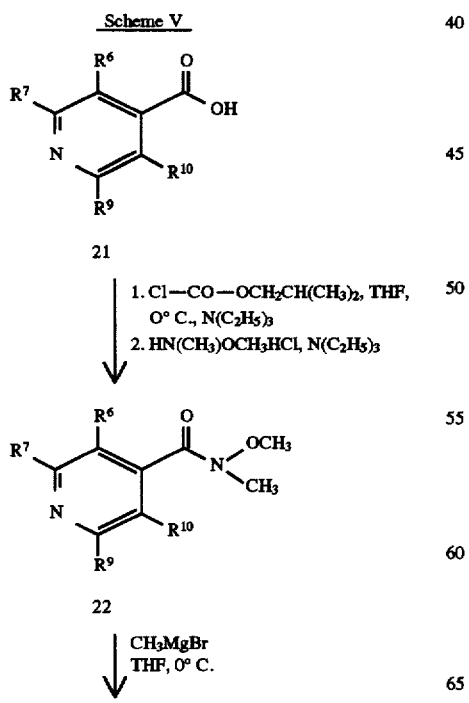

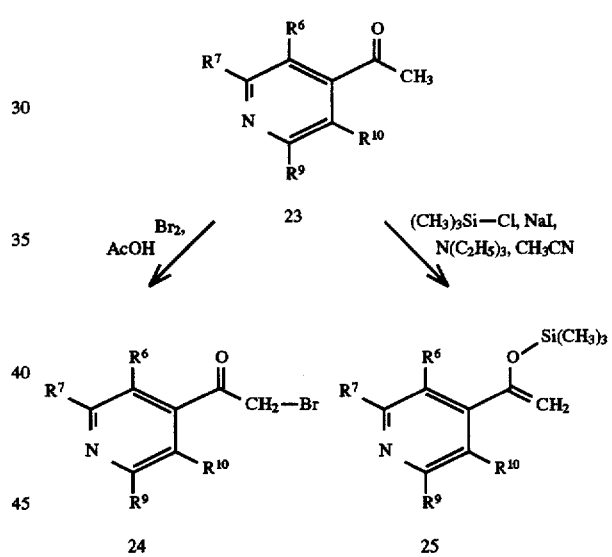

Synthetic Scheme V shows the three step procedure used to prepare the 4-(bromoacetyl)pyridines 24 and the 4-pyridinyl silyl enol ethers 25 from commercially available isonicotinic acids 21. In step one, a THF solution at of the isonicotinic acids 21 and two equivalents of triethylamine are sequentially treated with isobutyl chloroformate and N-hydroxymethyl-N-methylamine hydrochloride to give the Weinreb amides 22. In step two, the amides 22 are reacted with methylmagnesium bromide to give the corresponding 4-acetylpyridines 23. In step three, the 4-acetylpyridines 23 are either treated with bromine in acetic acid to give the corresponding 4-(bromoacetyl)pyridines 24 or chlorotrimethylsilane in acetonitrile in the presence of triethylamine and sodium iodide to give the corresponding 4-pyridinyl silyl enol ethers 25.

Scheme VI

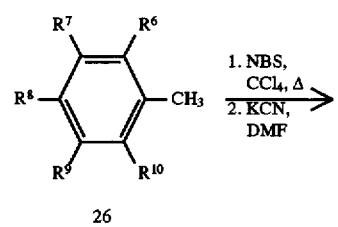
26

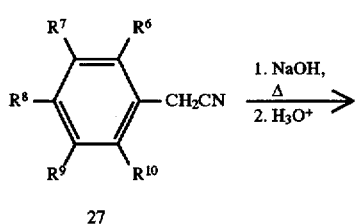
27

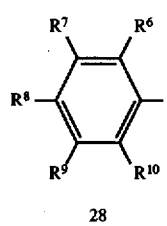
28

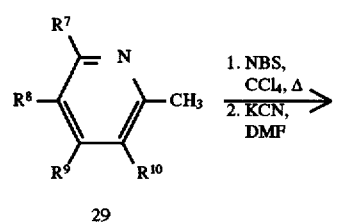
29

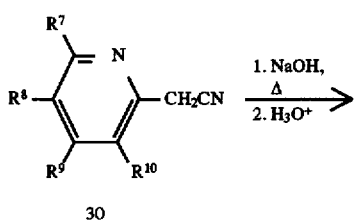
30

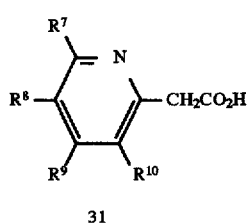
31

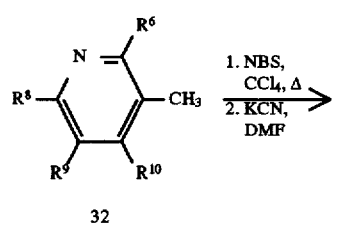
32

-continued
Scheme VI

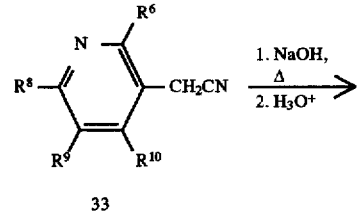
33

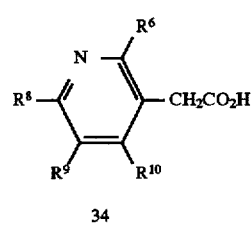
34

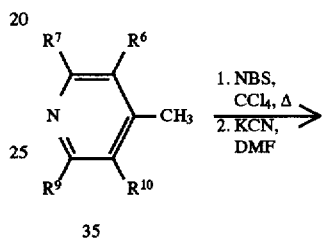
35

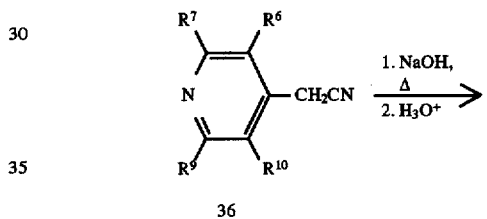
36

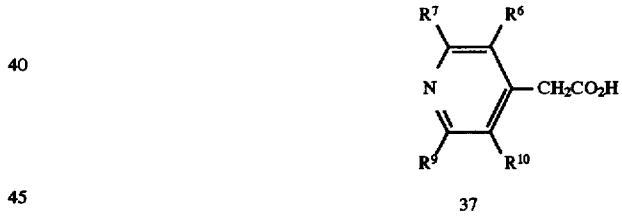
37

Synthetic Scheme VI shows the two step procedures which can be used to prepare the phenylacetic acids 28, 2-pyridinylacetic acids 31, 3-pyridinylacetic acids 34, and 4-pyridinylacetic acids 37 from commercially available toluenes 26, 2-picolines 29, 3-picolines 32, and 4-picolines 35, respectively. In step one, toluenes 26, 2-picolines 29, 3-picolines 32, and 4-picolines 35 are sequentially treated with N-bromosuccinimide (NBS) in carbon tetrachloride at reflux in the presence of a free radical initiator, e.g., 2,2'-azobis(2-methylpropionitrile) (AIBN), and potassium cyanide in DMF to give the corresponding phenylacetonitriles 27, 2-pyridinylacetonitriles 30, 3-pyridinylacetonitriles 33, and 4-pyridinylacetonitriles 36, respectively. In step two, phenylacetonitriles 27, 2-pyridinylacetonitriles 30, 3-pyridinylacetonitriles 33, and 4-pyridinylacetonitriles 36 are hydrolyzed with aqueous sodium hydroxide; acidification provides the phenylacetic acids 28, 2-pyridinylacetic acids 31, 3-pyridinylacetic acids 34, and 4-pyridinylacetic acids 37, respectively.

Scheme VII

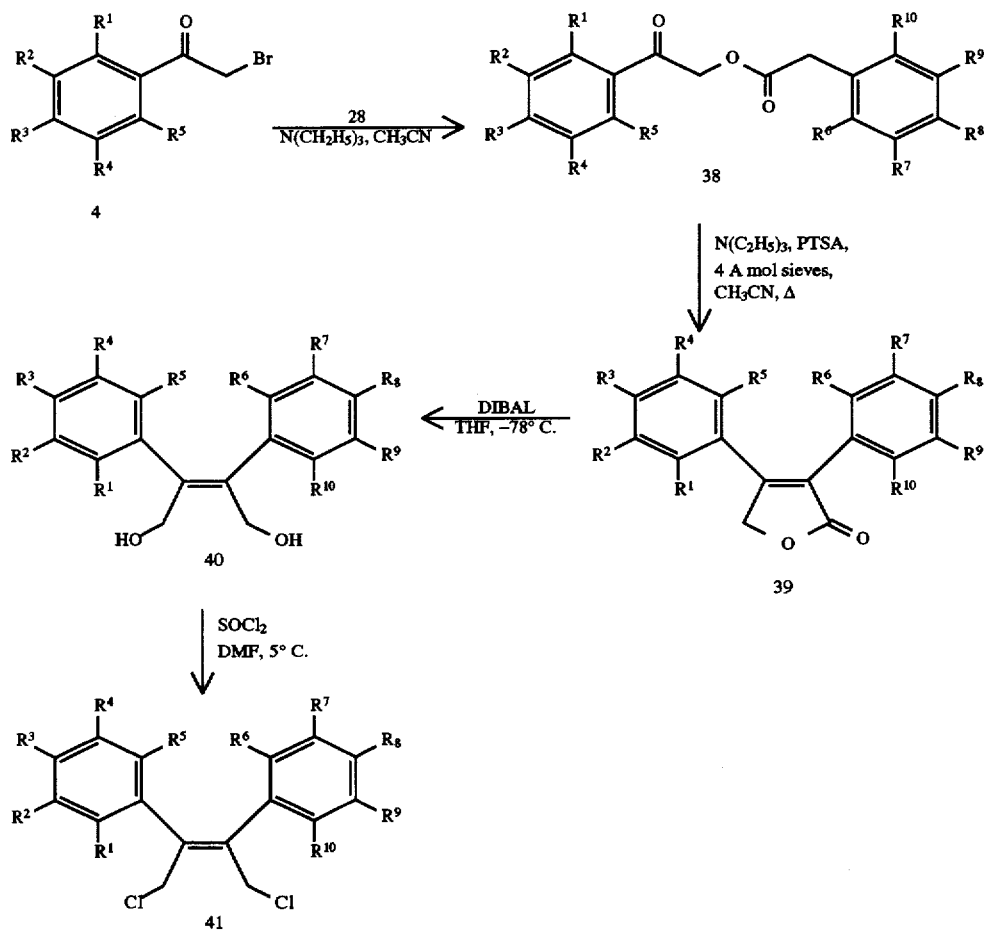

Synthetic Scheme VII shows the four step procedure used to prepare the cis-2,3-diaryl-1,4-dichloro-4-butenes 41 from the bromoacetophenones 4 (prepared in Synthetic Scheme I) and the phenylacetic acids 28 (prepared in Synthetic Scheme VI). In step one, bromoacetophenones 4 are reacted with phenylacetic acids 28 in acetonitrile in the presence of triethylamine to give the corresponding esters 38. In step two, the esters 38 are cyclized to the corresponding furanones 39 on treatment with p-toluenesulfonic acid (PTSA) and triethylamine in the presence of 4 Å molecular sieves in acetonitrile at reflux. In step three, the furanones 39 are reacted with diisobutylaluminum hydride (DIBAL) to give the corresponding cis-diols 40. In step four, the cis-diols 40 are reacted with thionyl chloride in DMF at 5° C. to give the corresponding cis-2,3-diaryl-1,4-dichloro-2-butenes 41.

Scheme VIII

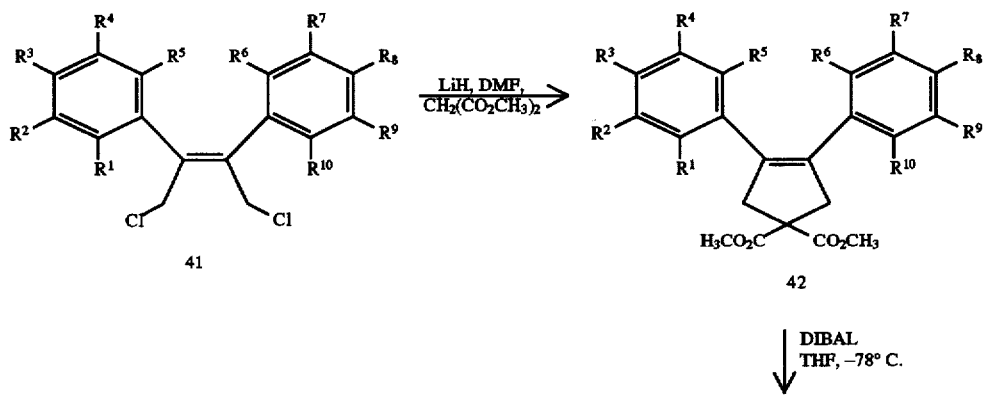

-continued
Scheme VIII

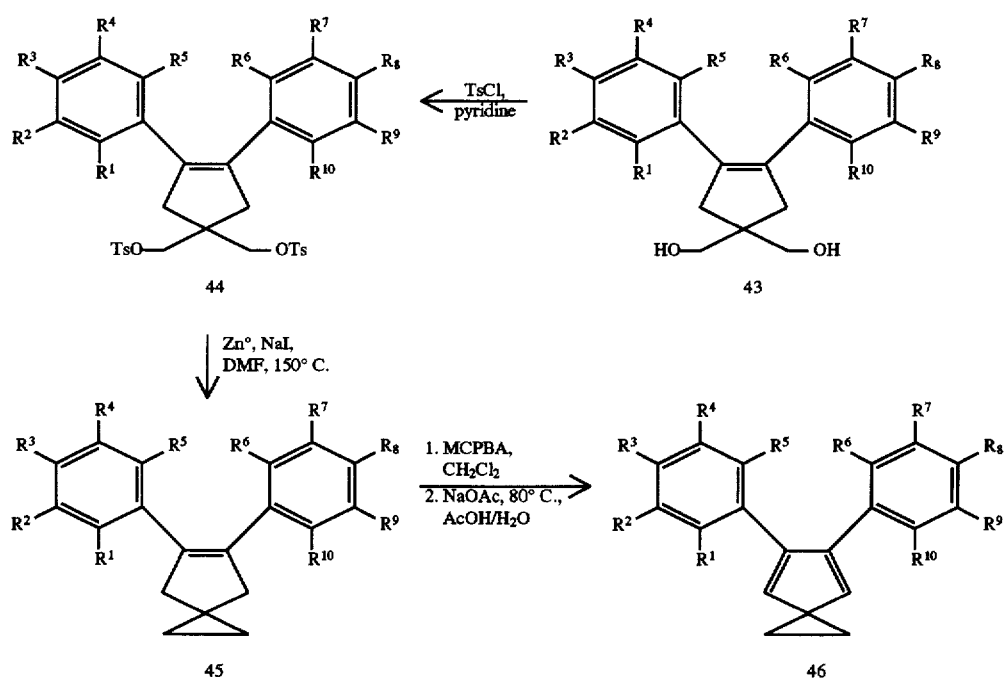

Synthetic Scheme VIII shows the five step procedure used to prepare the 5,6-diarylspiro[2.4]hepta-4,6-dienes 46 from the cis-2,3-diaryl-1,4-dichloro-2-butenes 41 (prepared in Synthetic Scheme VII). In step one, the cis-2,3-diaryl-1,4-dichloro-2-butenes 41 are reacted with dimethyl malonate in DMF in the presence of two equivalents of lithium hydride to give the corresponding 4,4-dicarbomethoxycyclopentenes 42. In step two, the 4,4-dicarbomethoxycyclopentenes 42 are reacted with DIBAL in THF to give the corresponding 4,4-di(hydroxymethyl)cyclopentenes 43. In step three, the 4,4-di(hydroxymethyl)cyclopentenes 43 are reacted with p-toluenesulfonyl chloride (TsCl) in pyridine to give the corresponding 4,4-ditosylates 44. In step four, the 4,4-ditosylates 44 are reacted with metallic zinc and sodium iodide in DMF at 150° C. to give 5,6-diarylspiro[2.4]hept-5-enes 45. In step five, the spiro[2.4]hept-5-enes 45 are first reacted with m-chloroperoxybenzoic acid (MCPBA) in methylene chloride at ambient temperature to give the corresponding epoxides which are subsequently reacted with sodium acetate in acetic acid/water (9:1) at 80° C. to give the 5,6-diarylspiro[2.4]hepta-4,6-diene antiinflammatory agents 46 of this invention.

Scheme IX

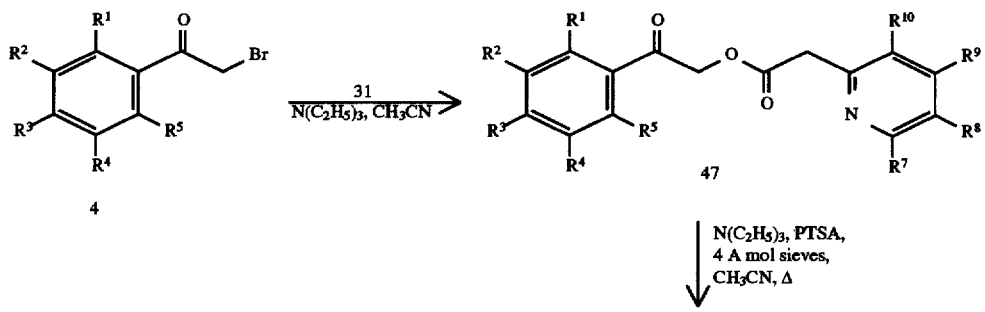

-continued
Scheme IX

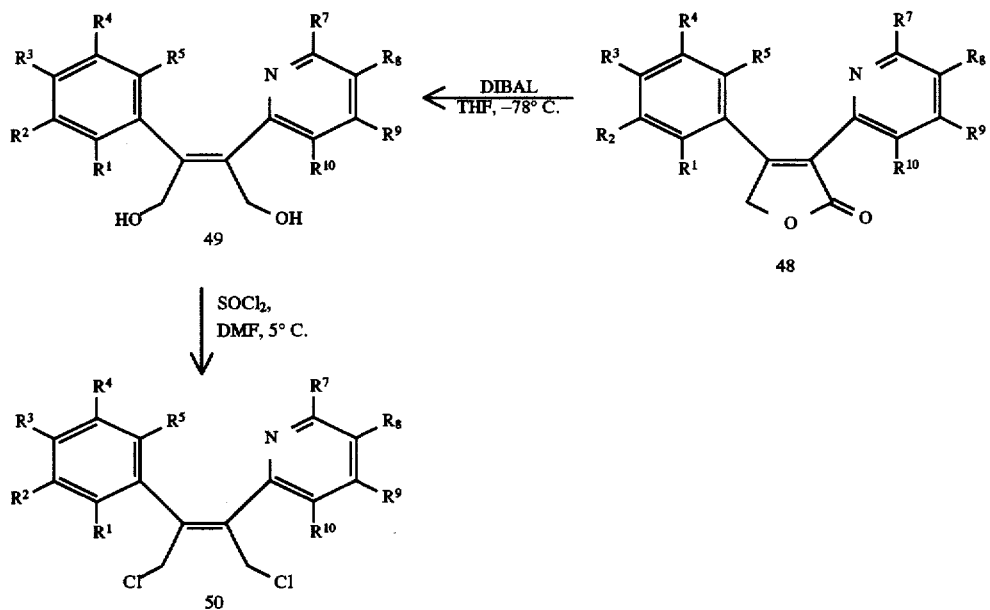

Synthetic Scheme IX shows the four step procedure used to prepare the cis-2-(2-pyridinyl)-3-aryl-1,4-dichloro-2-butenes 50 from the bromoacetophenones 4 (prepared in Synthetic Scheme I) and the 2-pyridinylacetic acids 31 (prepared in Synthetic Scheme VI). In step one, bromoacetophenones 4 are reacted with 2-pyridinylacetic acids 31 in acetonitrile in the presence of triethylamine to give the corresponding esters 47. In step two, the esters 47 are cyclized to the corresponding furanones 48 on treatment with p-toluenesulfonic acid (PTSA) and triethylamine in the presence of 4 Å molecular sieves in acetonitrile at reflux. In step three, the furanones 48 are reacted with diisobutylaluminum hydride (DIBAL) to give the corresponding cis-diols 49. In step four, the cis-diols 49 are reacted with thionyl chloride in DMF at 5° C. to give the corresponding cis-2-(2-pyridinyl)-3-aryl-1,4-dichloro-2-butenes 50.

Scheme X

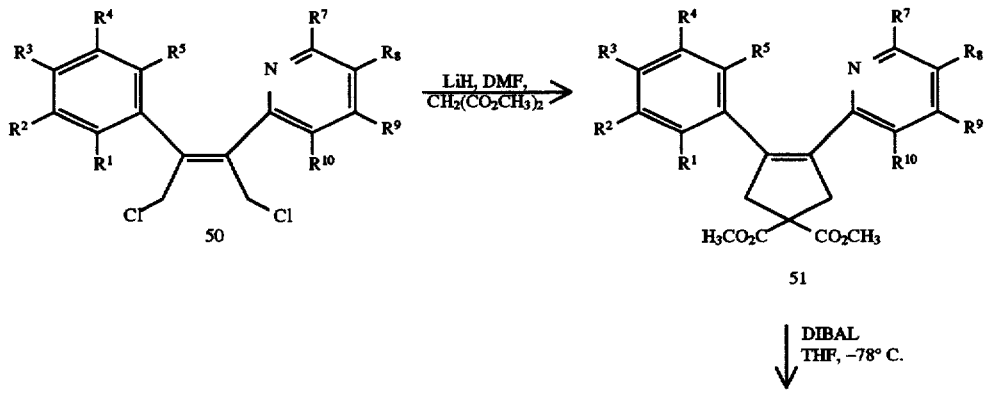

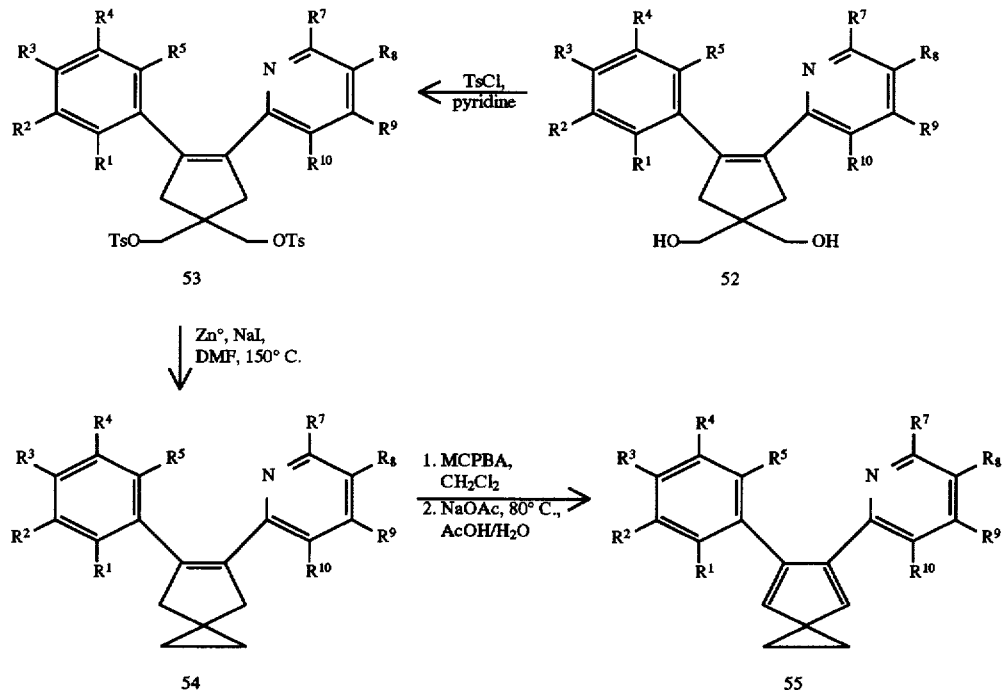

Synthetic Scheme X shows the five step procedure used to prepare the 5-(2-pyridinyl)-6-arylspiro[2.4]hepta-4,6-dienes 55 from the cis-2-(2-pyridinyl)-3-aryl-1,4-dichloro-2-butenes 50 (prepared in Synthetic Scheme IX). In step one, the cis-2-(2-pyridinyl)-3-aryl-1,4-dichloro-2-butenes 50 are reacted with dimethyl malonate in DMF in the presence of two equivalents of lithium hydride to give the corresponding 4,4-dicarbomethoxycyclopentenes 51. In step two, the 4,4-dicarbomethoxycyclopentenes 51 are reacted with DIBAL in THF to give the corresponding 4,4-di(hydroxymethyl)cyclopentenes 52. In step three, the 4,4-di(hydroxymethyl)cyclopentenes 52 are reacted with p-toluenesulfonyl chloride (TsCl) in pyridine to give the corresponding 4,4-ditosylates 53. In step four, the 4,4-ditosylates 53 are reacted with metallic zinc and sodium iodide in DMF at 150° C. to give 5-(2-pyridinyl)-6-arylspiro[2.4]hept-5-enes 54. In step five, the spiro[2.4]hept-5-enes 54 are first reacted with m-chloroperoxybenzoic acid (MCPBA) in methylene chloride at ambient temperature to give the corresponding epoxides which are subsequently reacted with sodium acetate in acetic acid/water (9:1) at 80° C. to give the 5-(2-pyridinyl)-6-arylspiro[2.4]hepta-4,6-diene antiinflammatory agents 55 of this invention.

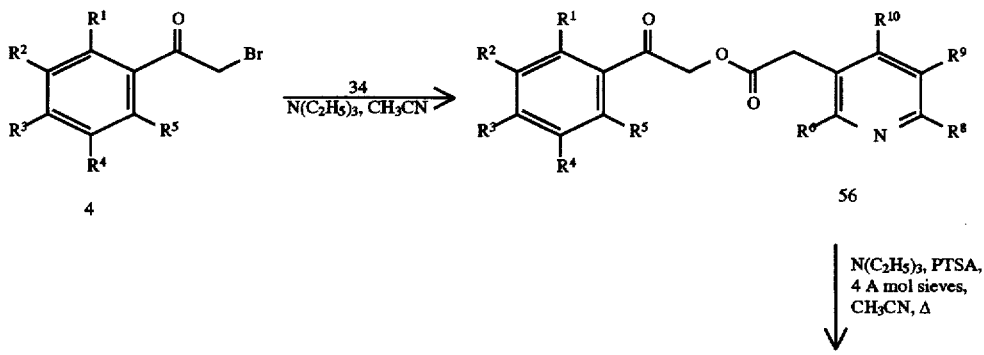

-continued
Scheme XI

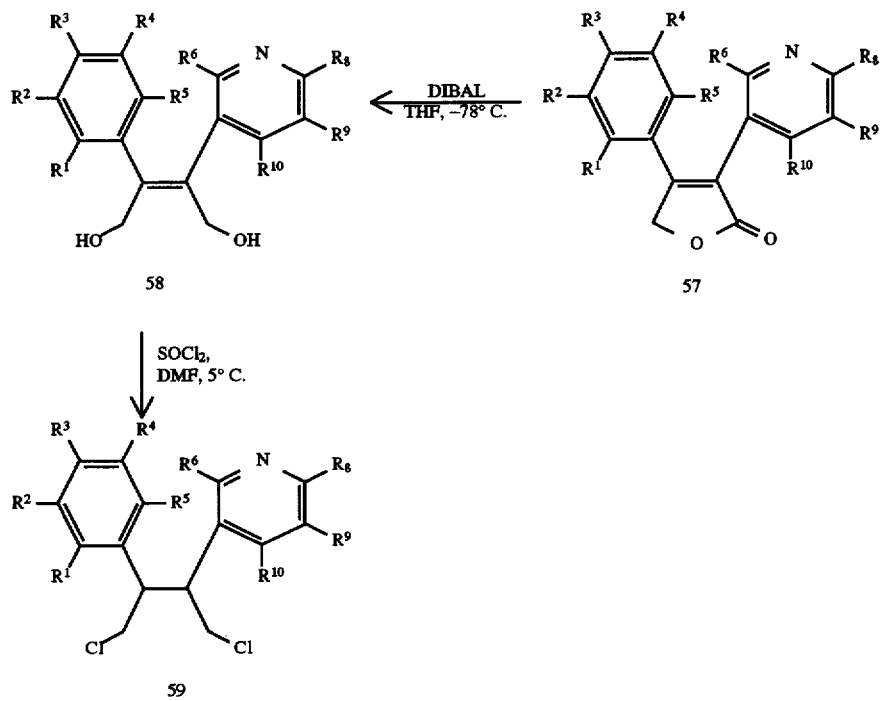

Synthetic Scheme XI shows the four step procedure used to prepare the cis-2-(3-pyridinyl)-3-aryl-1,4-dichloro-2-butenes 59 from the bromoacetophenones 4 (prepared in Synthetic Scheme I) and the 3-pyridinylacetic acids 34 (prepared in Synthetic Scheme VI). In step one, bromoacetophenones 4 are reacted with 3-pyridinylacetic acids 34 in acetonitrile in the presence of triethylamine to give the corresponding esters 56. In step two, the esters 56 are cyclized to the corresponding furanones 57 on treatment with p-toluenesulfonic acid (PTSA) and triethylamine in the presence of 4 Å molecular sieves in acetonitrile at reflux. In step three, the furanones 57 are reacted with diisobutylaluminum hydride (DIBAL) to give the corresponding cis-diols 58. In step four, the cis-diols 58 are reacted with thionyl chloride in DMF at 5° C. to give the corresponding cis-2-(3-pyridinyl)-3-aryl-1,4-dichloro-2-butenes 59.

Scheme XII

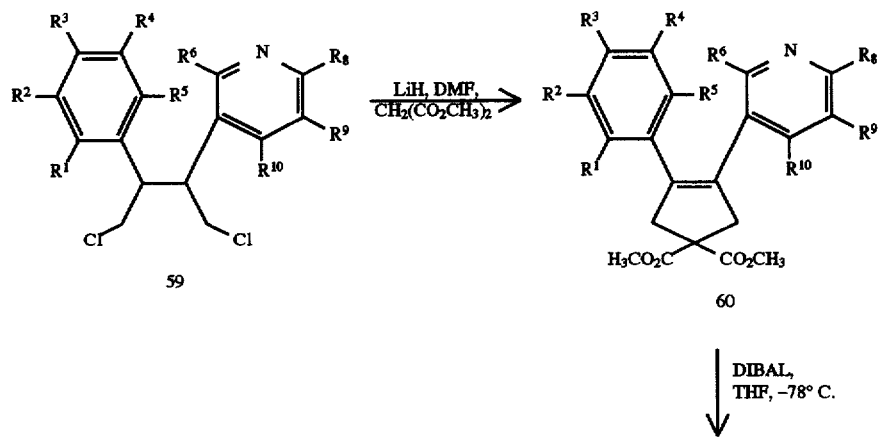

-continued
Scheme XII

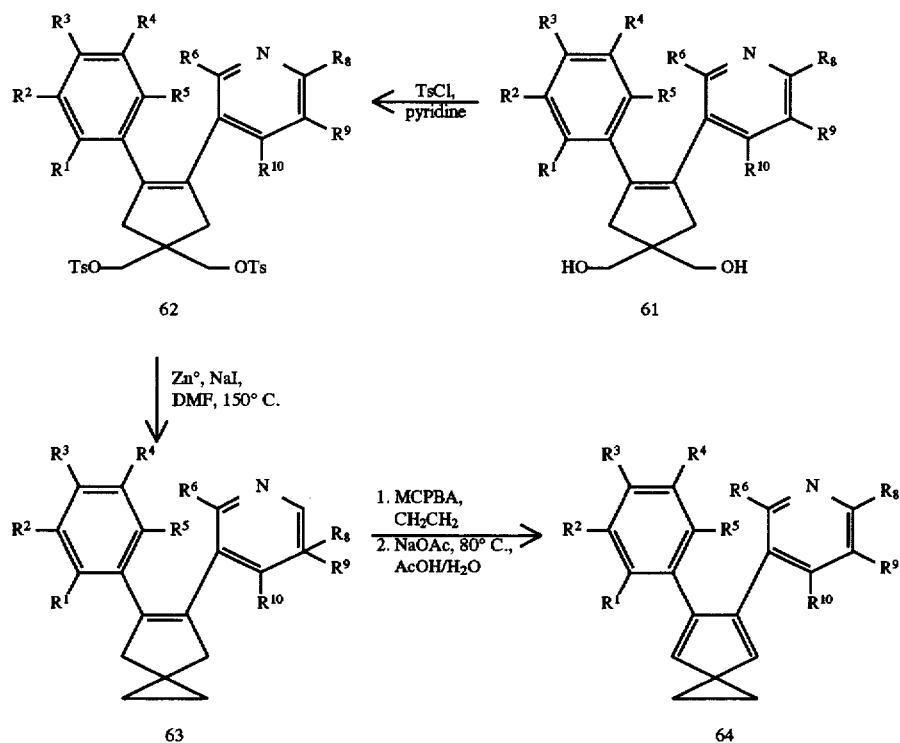

Synthetic Scheme XII shows the five step procedure used to prepare the 5-(3-pyridinyl)-6-arylspiro[2.4]hepta-4,6-dienes 64 from the cis-2-(3-pyridinyl)-3-aryl-1,4-dichloro-2-butenes 59 (prepared in Synthetic Scheme XI). In step one, the cis-2-(3 -pyridinyl)-3-aryl-1,4-dichloro-2-butenes 59 are reacted with dimethyl malonate in DMF in the presence of two equivalents of lithium hydride to give the corresponding 4,4-dicarbomethoxycyclopentenes 60. In step two, the 4,4-dicarbomethoxycyclopentenes 60 are reacted with DIBAL in THF to give the corresponding 4,4-di (hydroxymethyl) cyclopentenes 61. In step three, the 4,4-di (hydroxymethyl)cyclopentenes 61 are reacted with p-toluenesulfonyl chloride (TsCl) in pyridine to give the corresponding 4,4-ditosylates 62. In step four, the 4,4-ditosylates 62 are reacted with metallic zinc and sodium iodide in DMF at 150° C. to give 5-(3-pyridinyl)-6-arylspiro [2.4]hept-5-enes 63. In step five, the spiro[2.4]hept-5-enes 63 are first reacted with m-chloroperoxybenzoic acid (MCPBA) in methylene chloride at ambient temperature to give the corresponding epoxides which are subsequently reacted with sodium acetate in acetic acid/water (9:1) at 80° C. to give the 5-(3-pyridinyl)-6-arylspiro[2.4]hepta-4,6-diene antiinflammatory agents 64 of this invention.

Scheme XIII

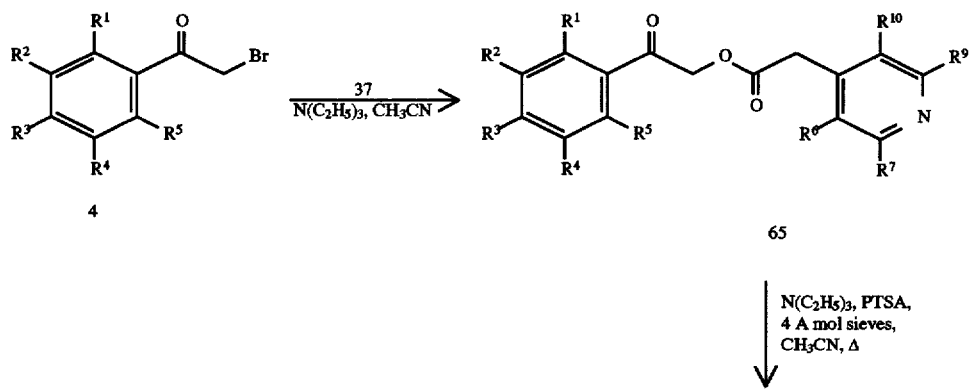

-continued
Scheme XIII

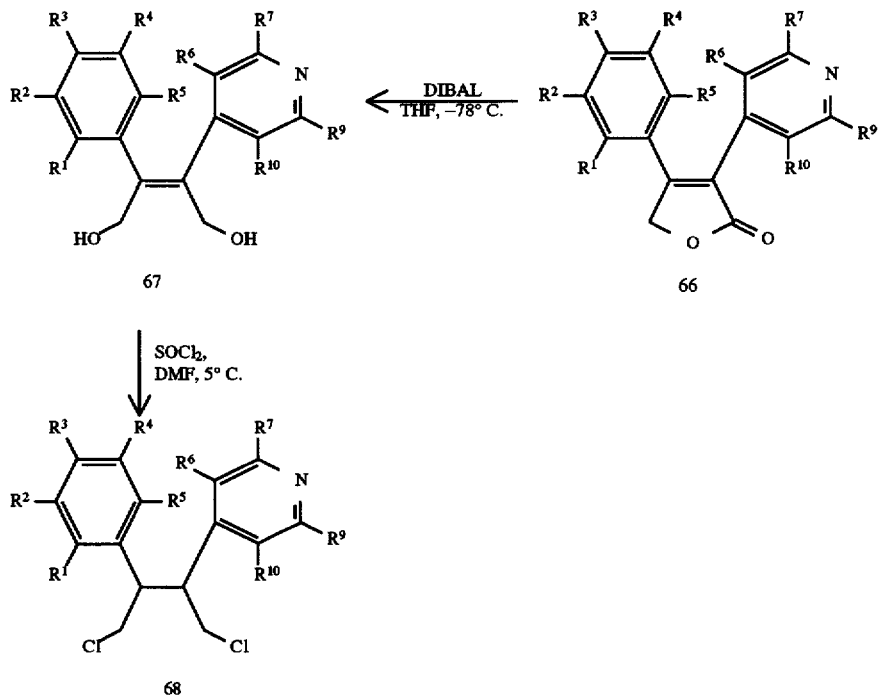

Synthetic Scheme XIII shows the four step procedure used to prepare the cis-2-(4-pyridinyl)-3-aryl-1,4-dichloro-2-butenes 68 from the bromoacetophenones 4 (prepared in Synthetic Scheme I) and the 4-pyridinylacetic acids 37 (prepared in Synthetic Scheme VI). In step one, bromoacetophenones 4 are reacted with 4-pyridinylacetic acids 37 in acetonitrile in the presence of triethylamine lo to give the corresponding esters 65. In step two, the esters 65 are cyclized to the corresponding furanones 66 on treatment with p-toluenesulfonic acid (PTSA) and triethylamine in the presence of 4 Å molecular sieves in acetonitrile at reflux. In step three, the furanones 66 are reacted with diisobutylaluminum hydride (DIBAL) to give the corresponding cis-diols 67. In step four, the cis-diols 67 are reacted with thionyl chloride in DMF at 5° C. to give the corresponding cis-2-(4-pyridinyl)-3-aryl-1,4-dichloro-2-butenes 68.

Scheme XIV

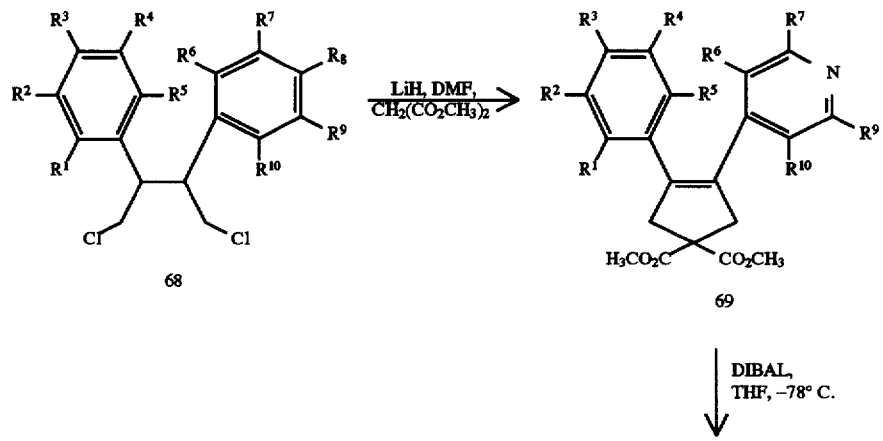

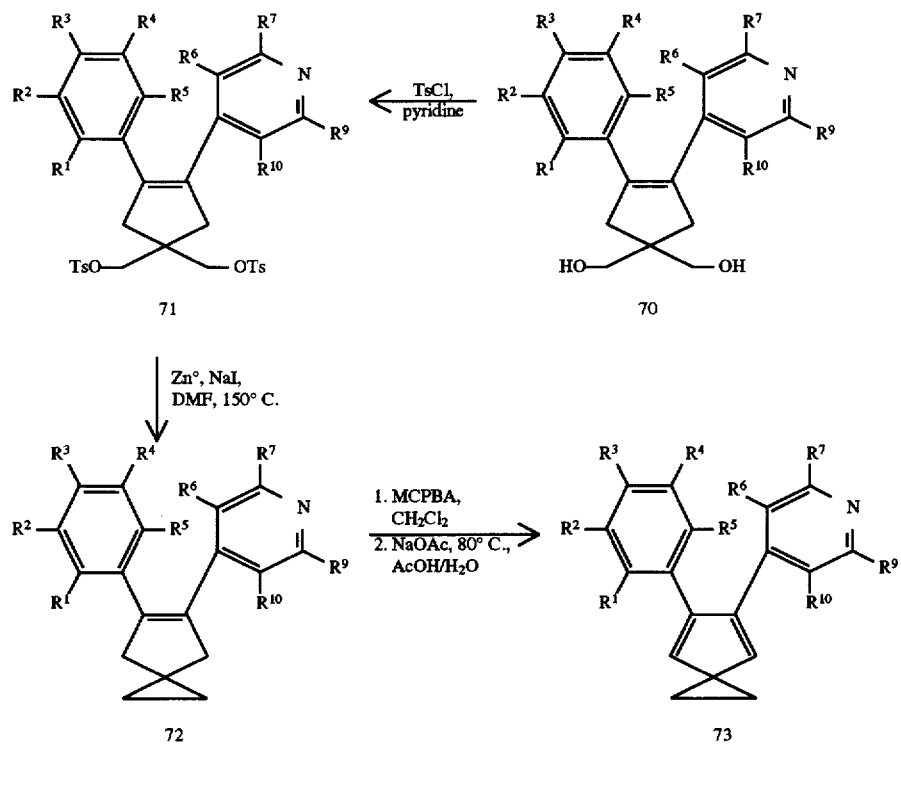

Synthetic Scheme XIV shows the five step procedure used to prepare the 5-(4-pyridinyl)-6-arylspiro[2.4]hepta-4,6-dienes 73 from the cis-2-(4-pyridinyl)-3-aryl-1,4-dichloro-2-butenes 68 (prepared in Synthetic Scheme XIII). In step one, the cis-2-(4-pyridinyl)-3-aryl-1,4-dichloro-2-butenes 68 are reacted with dimethyl malonate in DMF in the presence of two equivalents of lithium hydride to give the corresponding 4,4-dicarbomethoxycyclopentenes 69. In step two, the 4,4-dicarbomethoxycyclopentenes 69 are reacted with DIBAL in THF to give the corresponding 4,4-di(hydroxymethyl) cyclopentenes 70. In step three, the 4,4-di(hydroxymethyl)cyclopentenes 70 are reacted with p-toluenesulfonyl chloride (TsCl) in pyridine to give the corresponding 4,4-ditosylates 71. In step four, the 4,4-ditosylates 71 are reacted with metallic zinc and sodium iodide in DMF at 150° C. to give 5-(4-pyridinyl)-6-arylspiro[2.4]hept-5-enes 72. In step five, the spiro[2.4]hept-5-enes 72 are first reacted with m-chloroperoxybenzoic acid (MCPBA) in methylene chloride at ambient temperature to give the corresponding epoxides which are subsequently reacted with sodium acetate in acetic acid/water (9:1) at 80° C. to give the 5-(4-pyridinyl)-6-arylspiro[2.4]hepta-4,6-diene antiinflammatory agents 73 of this invention.

Scheme XV

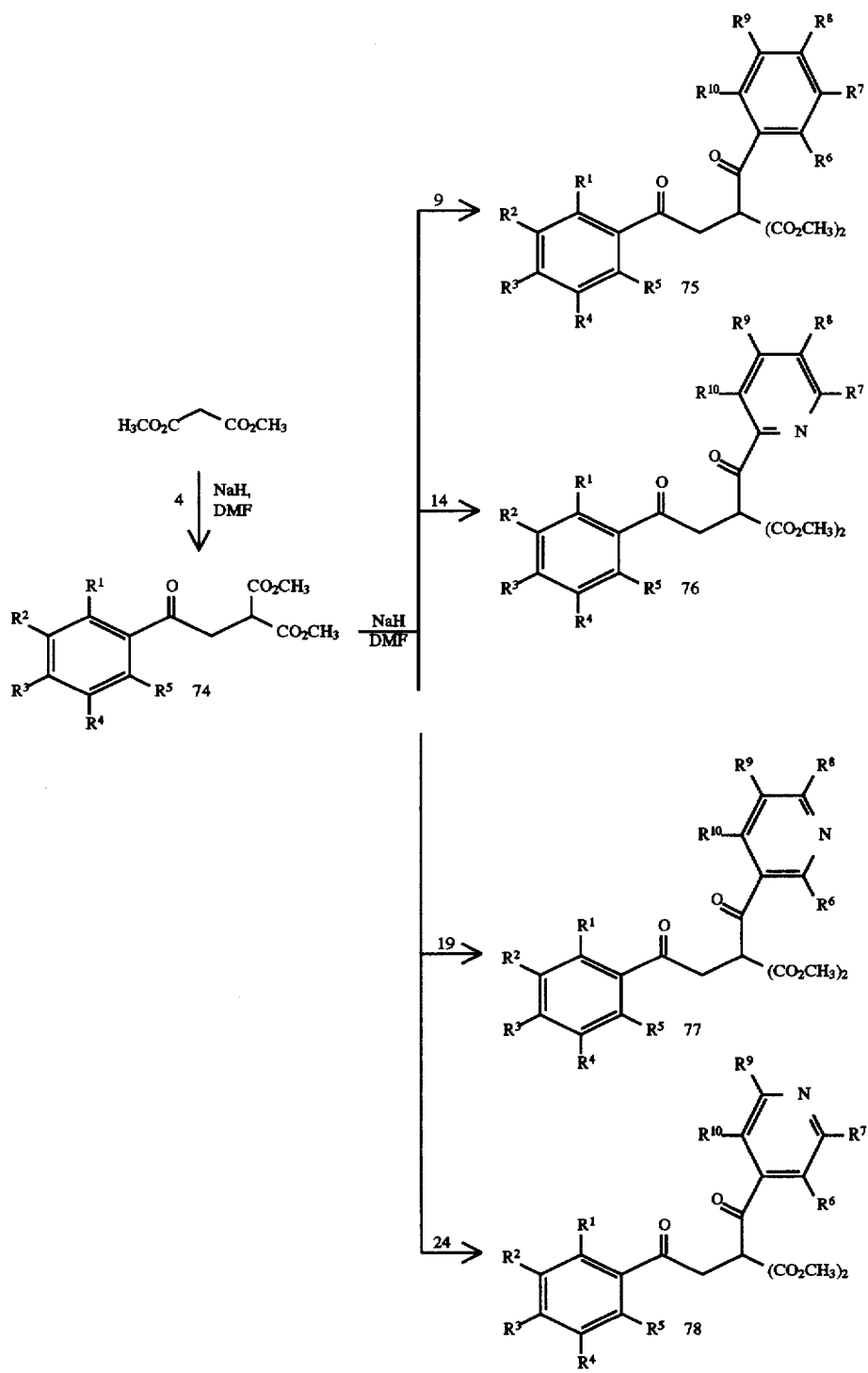

Synthetic Scheme XV shows a two step procedure which can be used to prepare the dialkylated compounds 75, 76, 77 and 78. In step one, dimethyl malonate and sodium hydride in DMF is reacted with the bromoacetophenones 4 (prepared in Synthetic Scheme I) to give the monoalkylated compounds 74. In step two, the monoalkylated compounds 74 are reacted with the bromoacetophenones 9 (prepared in Synthetic Scheme II), the 2-(bromoacetyl)pyridines 14 (prepared in Synthetic Scheme III), the 3-(bromoacetyl) pyridines 19 (prepared in Synthetic Scheme IV), and the 4-(bromoacetyl)pyridines 24 (prepared in Synthetic Scheme V) in DMF in the presence of sodium hydride to give the dialkylated compounds 75, 76, and 78, respectively.

Scheme XVI
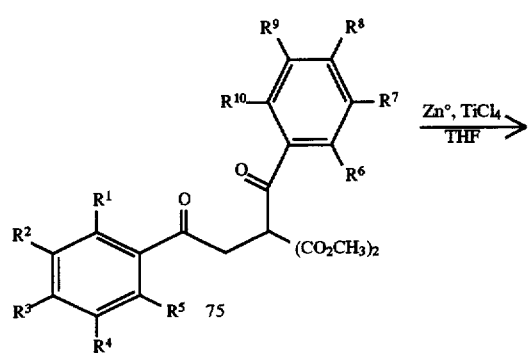
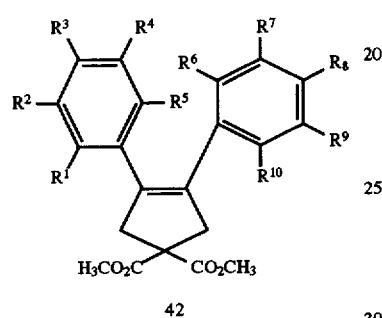
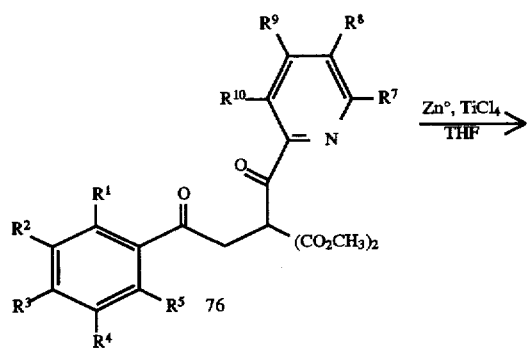
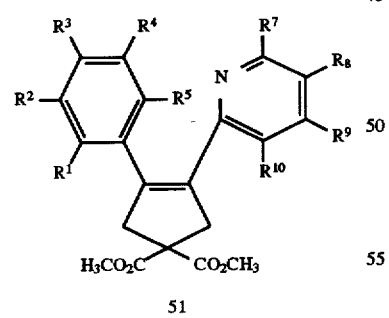
-continued
Scheme XVI
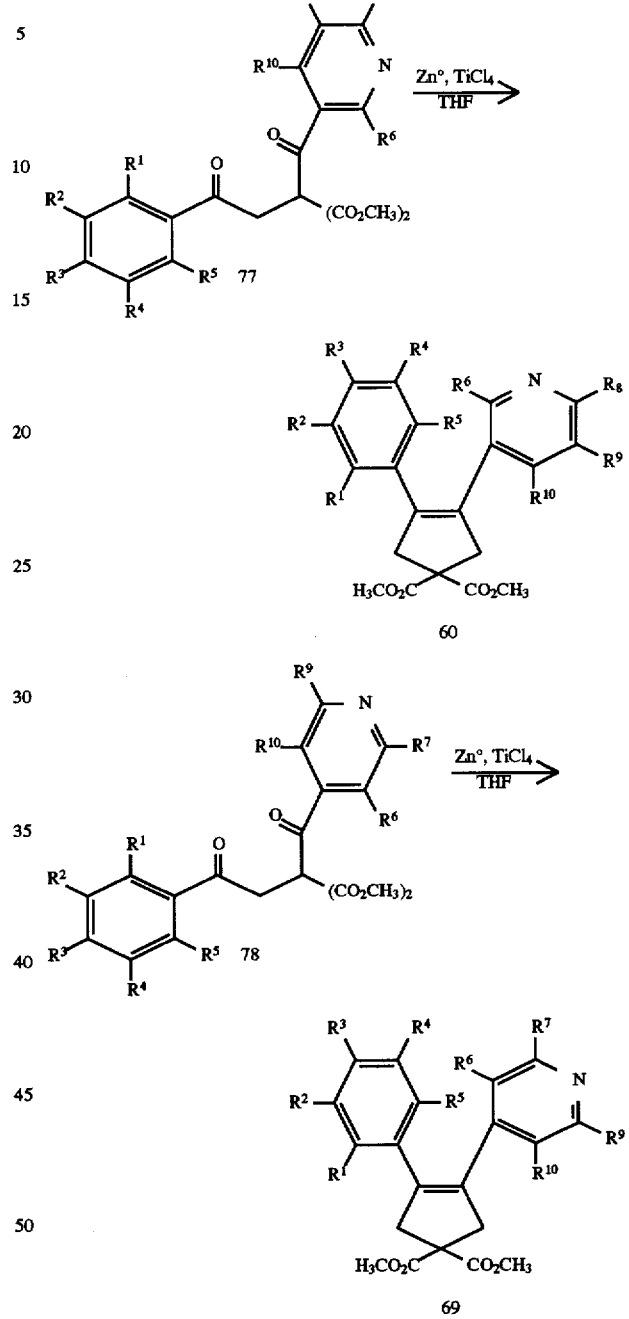
Synthetic Scheme XVI shows an alternative procedure which can be used to prepare the 4,4-dicarbomethoxycyclopentenes 42, 51, 60 and 69 from the dialkylated compounds 75, 76, 77 and 78, respectively (prepared in Synthetic Scheme XV). The dialkylated compounds 75, 76, 77 and 78 are reacted with metallic zinc and titanium(IV) chloride in THF to give the 4,4-dicarbomethoxycyclopentenes 42, 51, 60 and 69, respectively. By procedures outlined in Schemes VIII, X, XII, and XIV, 42, 51, 60, and 69 can be converted to the 5,6-diarylspiro[2.4]hepta-4,6-diene antiinflammatory agents 46, 5-(2-pyridinyl)-6-arylspiro[2.4]hepta-4,6-diene antiinflammatory agents 55, 5-(3-pyridinyl)-6-arylspiro[2.4]hepta-4,6-diene antiinflammatory agents 64, and 5-(4-pyridinyl)-6-arylspiro[2.4]hepta-4,6-diene antiinflammatory agents 73, respectively, of this invention.

Synthetic Scheme XVII shows the three step procedure used to prepare the cycloalkyldiketones 81, 82, and 84 from the phenyl silyl enol ethers 5 (prepared in Synthetic Scheme I) and cycloalkanones (n=1,2). In step one, the silyl enol ethers 5 are reacted with cycloalkanones (n=1,2) in methylene chloride in the presence of titanium(IV) chloride to give the corresponding cycloalkanols 79. In step two, the cycloalkanols 79 are dehydrated with trifluoroacetic anhydride and triethylamine in methylene chloride at 0° C. to give the corresponding conjugated exocyclic olefins 80. In step three, the olefins 80 are reacted with the phenyl silyl Scheme XVII

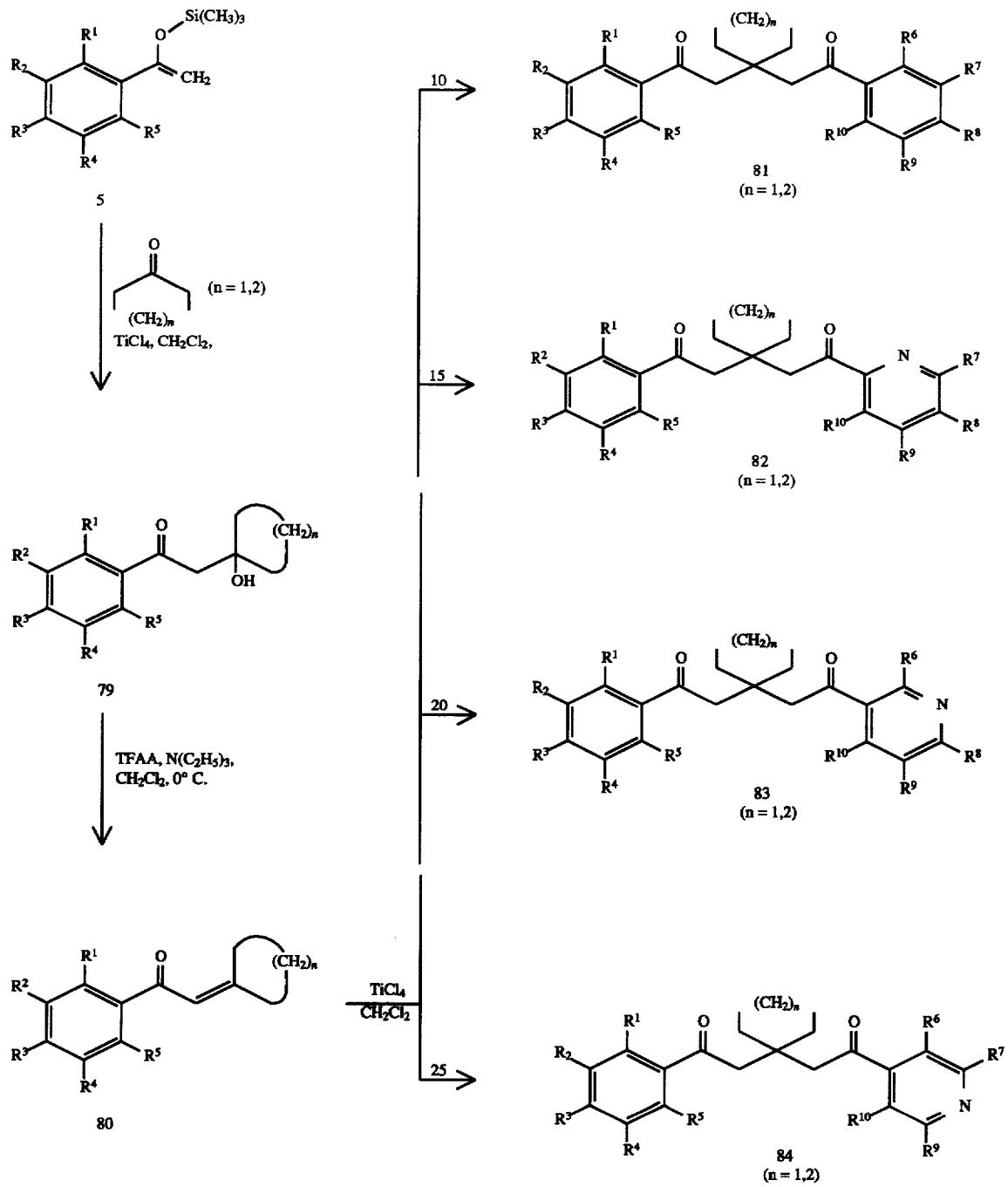

enol ethers 10 (prepared in Synthetic Scheme II), 2-pyridinyl silyl enol ethers 15 (prepared in Synthetic Scheme III), 3-pyridinyl silyl enol ethers 20 (prepared in Synthetic Scheme IV), and 4-pyridinyl silyl enol ethers 25 (prepared in Synthetic Scheme V) to give the cycloalkyldiketones (n=1,2) 81, 82, 83 and 84, respectively.

(n=1,2) 81, 89, 83 and respectively (prepared in Synthetic Scheme XVII). The cycloalkyldiketones (n=1,2) 81, 89, 83 and 84 are reacted with metallic zinc and titanium(IV) chloride in THF to give 6,7-diarylspiro[3.4]oct-6-enes 85 (n=1) and 2,3-diarylspiro[4.4]non-2-enes 85 (n=2), 6-(2-pyridinyl)-7-arylspiro[3.4]oct-6-enes 86 (n=1) and 2-(2-

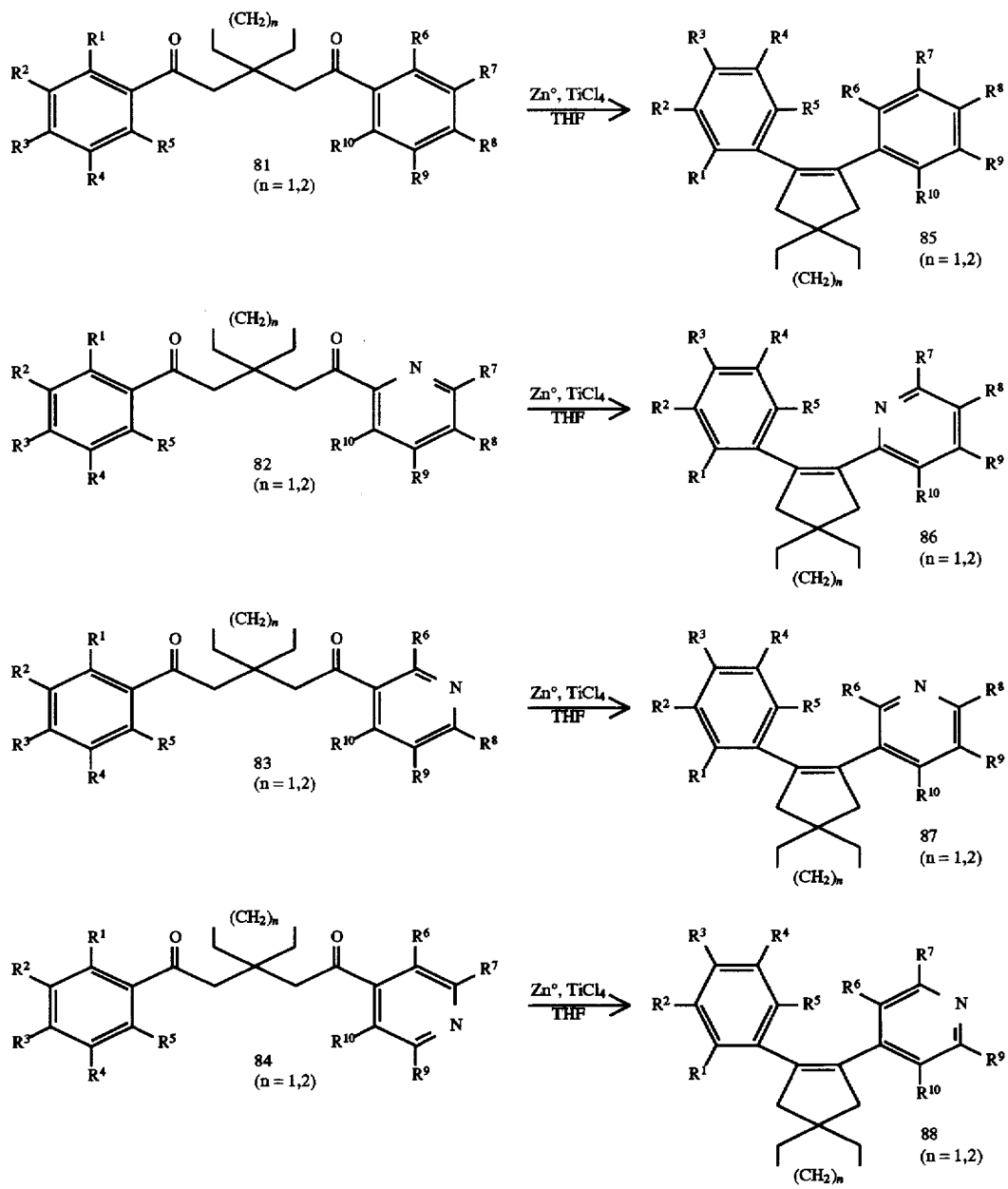

Scheme XVIII

Synthetic Scheme XVIII shows the procedures used to prepare 6,7-diarylspiro[3.4]oct-6-enes 85 (n=1) and 2,3-diarylspiro[4.4]non-2-enes 85 (n=2), 6-(2-pyridinyl)-7-arylspiro[3.4]oct-6-enes 86 (n=1) and 2-(2-pyridinyl)-3-arylspiro[4.4]non-2-enes 86 (n=2), 6-(3-pyridinyl)-7-arylspiro[3.4]oct-6-enes 87 (n=1) and 2-(3-pyridinyl)-3-arylspiro[4.4]non-2-enes 87 (n=2), and 6-(4-pyridinyl)-7-arylspiro[3.4]oct-6-enes 88 (n=1) and 2-(4-pyridinyl)-3-arylspiro[4.4]non-2-enes 88 (n=2) from cycloalkyldiketones pyridinyl)-3-arylspiro[4.4]non-2-enes 86 (n=2), the 6-(3-pyridinyl)-7-arylspiro[3.4]oct-6-enes 87 (n=1) and 2-(3-pyridinyl)-3-arylspiro[4.4]non-2-enes 87 (n=2), and the 6-(4-pyridinyl)-7-aryl spiro[3.4]oct-6-enes 88 (n=1) and 2-(4-pyridinyl)-3-arylspiro[4.4]non-2-enes 88 (n=2), respectively.

Scheme XIX

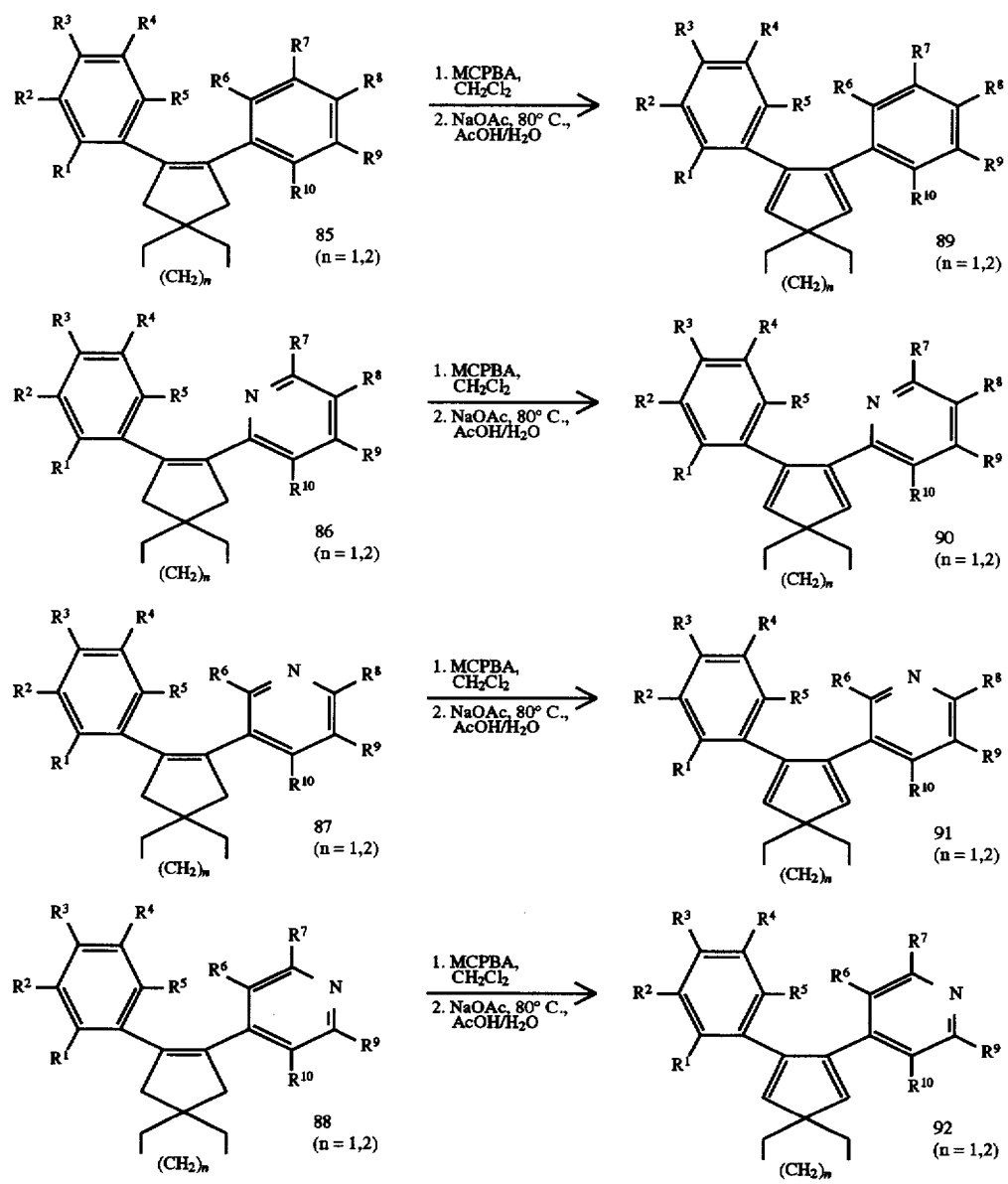

Synthetic Scheme XIX shows the procedures which can be used to prepare 6,7-diarylspiro[3.4]octa-5,7-dienes 89 (n=1) and 2,3-diarylspiro[4.4]nona-1,3-dienes 89 (n=2), 6-(2-pyridinyl)-7-arylspiro[3.4]octa-5,7-dienes 90 (n=1) and 2-(2-pyridinyl)-3-arylspiro[4.4]nona-1,3-dienes 90 (n=2), 6-(3-pyridinyl)-7-arylspiro[3.4]octa-5,7-dienes 91 (n=1) and 2-(3-pyridinyl)-3 -arylspiro[4.4]nona-1,3-dienes 91 (n=2), and 6-(4-pyridinyl)-7-arylspiro[3.4]octa-5,7-dienes 92 (n=1) and 2-(4-pyridinyl)-3-arylspiro[4.4]nona-1,3-dienes 92 (n=2) from 85, 86, 87 and 88, respectively (prepared in Synthetic Scheme XVIII). The spirocyclopentenes 85, 86, 87 and 88 are first reacted with m-chloroperoxybenzoic acid (MCPBA) in methylene chloride at ambient temperature to give the corresponding epoxides which are subsequently reacted with sodium acetate in acetic acid/water (9:1) at 80° C. to give the 6,7-diarylspiro[3.4]octa-5,7-diene antiinflammatory agents 89 (n=1) and 2,3-diarylspiro [4.4]non-1,3-diene antiinflammatory agents 89 (n=2), 6-(2-pyridinyl)-7-arylspiro[3.4] octa-5,7-diene antiinflammatory agents 90 (n=1) and 2-(2-pyridinyl)-3-arylspiro [4.4]nona-1,3-diene antiinflammatory agents 90 (n=2), 6-(3-pyridinyl)-7-arylspiro[3.4]octa-5,7-diene antiinflammatory agents 91 (n=1) and 2-(3-pyridinyl) -3-arylspiro [4.4]nona-1,3-diene antiinflammatory agents 91 (n=2), and 6-(4-pyridinyl)-7-arylspiro[3.4]octa-5,7-diene antiinflammatory agents 99. (n=1) and 2-(4-pyridinyl)-3-arylspiro[4.4]nona-1,3-diene antiinflammatory agents 99. (n=2), respectively, of this invention.

Scheme XX

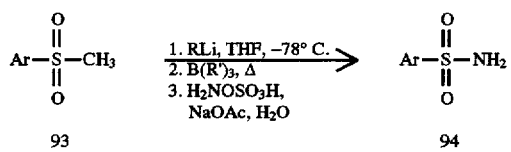

Synthetic Scheme XX shows the three step procedure used to prepare sulfonamide antiinflammatory agents 93 from their corresponding methylsulfones 93. In step one, a THF solution of the methylsulfones 93 at −78° C. are treated with an alkyllithium reagent, e.g., methyllithium, n-butyllithium, etc. In step two, the anions generated in step one is treated with an organoborane, e.g., triethylborane, tributylborane, etc., at −78° C. then allowed to warm to ambient temperature prior to stirring at reflux. In step three, an aqueous solution of sodium acetate and hydroxyamine-O-sulfonic acid is added to provide the corresponding sulfonamide antiinflammatory agents 94 of this invention.

The following examples contain detailed descriptions of the methods of preparation of compounds of Formula I–VI. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

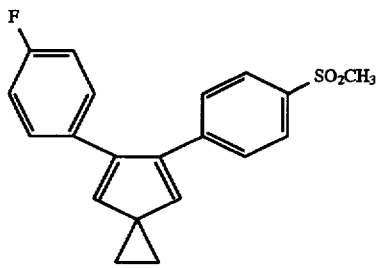

Step 1

5-(4-Fluorophenyl)-6-[4-(methylsulfonyl)phenyl]spiro[2.4]hepta-4,6-diene

To a stirred solution of 50 g (340 mmol) of 4-(methylthio)benzonitrile in 2 L of THF at −78° C. under an atmosphere of nitrogen was added 282 mL (390 mmol) of methyllithium (1.4M in diethyl ether) over a period of ten minutes. The solution was stirred at −78° C. for one hour, and then the dry ice bath was removed. After five hours, 100 mL of water followed by 200 mL of 3N hydrochloric acid were added to the reaction mixture and it was stirred overnight. Concentration in vacuo gave a residue which was partitioned between ethyl acetate and water. The water layer was extracted with three portions of ethyl acetate and the combined ethyl acetate layers were dried ($MgSO_4$). Concentration in vacuo gave 58 g of crude (4-methylthio)acetophenone as a solid: NMR ($CDCl_3$) δ2.52 (s, 3H), 2.57 (s, 3H), 7.26 (d, J=9 Hz, 2H), 7.87 (d, J=9 Hz, 2H).

Step 2

Preparation of 4-(methylsulfonyl)acetophenone

To a solution of 11.73 g (71.1 mmol) of 4-(methylsulfonyl)acetophenone (prepared in Step 1) in 500 mL of dichloromethane at ambient temperature was added 61.14 g (177 mmol) of m-chloroperoxybenzoic acid (50%) (MCPBA) in portions over 20 minutes. The reaction was stirred for two hours, quenched slowly with aqueous sodium bisulfite, washed with three 100 mL portions of saturated sodium bicarbonate, dried ($MgSO_4$), and concentrated in vacuo to give 11.91 g (91%) of (4-methylsulfonyl) acetophenone as a colorless solid: NMR ($CDCl_3$) δ2.67 (s, 3H), 3.08 (s, 3H), 8.06 (d, J=9 Hz, 2H), 8.14 (d, J=9 Hz, 2H).

Step 3

Preparation of 2-bromo-4'-(methylsulfonyl)acetophenone

To a stirred solution of 11.91 g (60.5 mmol) of 4-(methylsulfonyl)acetophenone (prepared in Step 2) in 133 mL of glacial acetic acid and 0.11 mL of hydrochloric acid at ambient temperature was added a solution of 8.22 g (51.4 mmol) of bromine in 9.3 mL of glacial acetic acid over a period of three hours. The reaction mixture was diluted with 500 mL of water and extracted with chloroform. The combined extracts were dried ($MgSO_4$) and concentrated in vacuo to give 15.7 g of crude 2-bromo-(4'-methylsulfonyl)acetophenone as a solid: NMR ($CDCl_3$) δ3.10 (s, 3H), 4.45 (s, 2H), 8.08 (d, J=9 Hz, 2H), 8.17 (d, J=9 Hz, 2H).

Step 4

Preparation of 2-(4-fluorophenyl)-1-[2-[4-(methylsulfonyl)phenyl]-2-oxoethoxy]ethanone To a stirred solution of 4.45 g (28.9 mmol) of 4-fluorophenylacetic acid in 3.26 g (31.8 mmol) of triethylamine and 275 mL of acetonitrile was added 8.9 g (28.9 mmol) of 2-bromo-4'-(methylsulfonyl)acetophenone (prepared in Step 3) at ambient temperature. The reaction mixture was stirred for 30 minutes, concentrated in vacuo, and partitioned between ethyl acetate and water. The organic phase was dried ($MgSO_4$) and concentrated in vacuo. Purification by silica gel chromatography with ethyl acetate/hexane (1:1) gave 6.87 g (68%) of 2-(4-fluorophenyl)-1-[2-[4-(methylsulfonyl)phenyl]-2-oxoethoxy]ethanone as a colorless solid: NMR ($CDCl_3$) δ3.08 (s, 3H), 3.79 (s, 2H), 5.35 (s, 2H), 7.06 (s, n, J=9 Hz, 2H), 7.32 (dd, J=6 and 9 Hz, 2H), 8.06 (s, 4H).

Step 5

Preparation of 3-(4-fluorophenyl)-4-[(4-methylsulfonyl)phenyl]-5H-furan-2-one

Under nitrogen, 4.10 g (11.7 mmol) of 2-(4-fluorophenyl)-1-[2-[4-(methylsulfonyl)phenyl]-2-oxoethoxy]ethanone (prepared in Step 4), 6.52 mL (46.8 mmol) of triethylamine, 4.89 g (25.7 mmol) of p-toluenesulfonic acid, and 12 g of 4 Å molecular sieves were added to 117 mL of acetonitrile and stirred at reflux for 16 hours. The reaction mixture was concentrated in vacuo and the residue partitioned between dichloromethane and water. The dichloromethane layer was dried ($MgSO_4$) and reconcentrated in vacuo. Recrystallization from hexane/ethyl acetate (2:1) gave 3.65 g (94%) of 3-(4-fluorophenyl)-4-[(4-methylsulfonyl)phenyl]-5H-furan-2-one as a solid: mp 166°–167° C.; NMR ($CDCl_3$) δ3.08 (s, 3H), 5.19 (s, 2H), 7.10 (t, J=9 Hz, 2H), 7.42 (dd, J=6 and 9 Hz, 2H), 7.52 (d, J=9 Hz, 2H), 7.97 (d, J=9 Hz, 2H). HRMS. Calc'd for $C_{17}H_{13}FO_4S$: 332.0519. Found: 332.0501. Anal. Calc'd for $C_{17}H_{13}FO_4S$: C, 61.44; H, 3.94; O, 19.26. Found: C, 61.11; H, 4.06; O, 19.32.

Step 6

Preparation of 2-(4-fluorophenyl)-3-[(4-methylsulfonyl)phenyl]-1,4-dihydroxy-2-butene To a solution of 3.08 g (9.28 mmol) of 3-(4-fluorophenyl)-4-[(4-methylsulfonyl)phenyl]-5H-furan-2-one (prepared in Step 5) in 93 mL of tetrahydrofuran (THF) at −78° C. under an atmosphere of nitrogen was added 20 mL (30 mmol) of diisobutylaluminum hydride (DIBAL) (1.5M in THF) over a 10 minute period. The solution was stirred at −78° C. for 20 minutes, allowed to warm to ambient temperature, and stirred overnight. An additional 15 mL (22 mmol) aliquot of DIBAL was added and stirring was continued for 2 hours. The reaction was cooled to −78° C., treated dropwise with 25 mL of acetone, warmed to room temperature, and slowly treated with 25 mL of water. The mixture was stirred for 30 minutes prior to the careful addition of 35 mL of 1.2N sodium hydroxide. The mixture was extracted with ethyl acetate, washed with 1N hydrochloric acid followed by brine, dried (MgSO$_4$), and concentrated in vacuo to give 3.8 g of crude 2-(4-fluorophenyl)-3-[(4-methylsulfonyl) phenyl]-1,4-dihydroxy-2-butene as a colorless oil: NMR (CDCl$_3$) δ2.98 (s, 3H), 4.60 (d, J=6 Hz, 4H), 6.8 (t, J=9 Hz, 2H), 6.94–7.02 (m, 2H), 7.22 (d, J=9 Hz, 2H), 7.65 (d, J=9 Hz, 2H).

Step 7

Preparation of 2-(4-fluorophenyl)-3-[(4-methylsulfonyl)phenyl]-1,4-dichloro-2-butane To a solution of 3.5 g (7.62 mmol) of crude 2-(4-fluorophenyl)-3-[(4-methylsulfonyl)phenyl]-1,4-dihydroxy-2-butene (prepared in Step 6) in 58 mL of N,N-dimethylformamide (DMF) at 5° C. under an atmosphere of nitrogen was added dropwise 1.52 mL (20.84 mmol) of thionyl chloride. The reaction was stirred at 5° C. for 22 hours, stirred at ambient temperature for an additional 8 hours, and concentrated in vacuo. The residue was partitioned between ethyl acetate and water; the ethyl acetate phase was dried (MgSO$_4$) and concentrated in vacuo to give crude 2-(4-fluorophenyl)-3-[(4-methylsulfonyl)phenyl]-1,4-dichloro-2-butene as a solid: NMR (CDCl$_3$) δ3.0 (s, 3H), 4.55 (d, J=3.4 Hz, 4H), 6.86 (t, J=9 Hz, 2H), 6.75 (d, J=8.3 Hz, 2H), 7.45 (d, J=9 Hz, 2H).

Step 8, A

Preparation of 1-[2-(4-fluorophenyl)-4,4-dicarbomethoxycyclopenten-1-yl]-4-(methylsulfonyl)benzene To a solution of 1.2 mL (10.5 mmol) of dimethyl malonate in 10 mL of DMF under an atmosphere of nitrogen was added 215 mg (26.9 mmol) of lithium hydride in portions. The resulting suspension was stirred at ambient temperature for 20 minutes prior to the addition of a solution of crude 2-(4-fluorophenyl)-3-[(4-methylsulfonyl)phenyl]-1,4-dichloro-2-butene (prepared in Step 7) in 10 mL of DMF. The reaction was stirred at ambient temperature for 15 hours, treated with another 150 mg (18.8 mmol) of lithium hydride, and stirred for another 4 hours. The mixture was concentrated in vacuo and partitioned between ethyl acetate and water; the organic phase was dried (MgSO$_4$), and concentrated in vacuo. The residue was chromatographed on silica gel to give 1.1 g (34%) of 1-[2-(4-fluorophenyl)-4,4-dicarbomethoxycyclopenten-1-yl]-4-(methylsulfonyl)benzene as an oil: NMR (CDCl$_3$) a 3.03 (s, 3H), 3.55 (s, 4H), 3.79 (s, 6H), 6.93 (t, J=9 Hz, 2H), 7.11 (dd, J=6 and 9 Hz, 2H), 7.32 (d, J=9 Hz, 2H), 7.77 (d, J=9 Hz, 2H).

Step 8, B

Preparation of 1-[2-(4-fluorophenyl)-4,4-dicarbomethoxycyclopenten-1-yl]-4-(methylsulfonyl)benzene To a solution of 7.18 mL (63 mmol) of dimethyl malonate in 160 mL of DMF an 0° C. under an atmosphere of nitrogen was added 3.0 g (75 mmol) of sodium hydride (60% suspension in oil). The reaction was stirred at ambient temperature for 15 minutes (or until the gas evolution has ceased), cooled to −20° C., and treated with 15 g (69 mmol) of 2-bromo-4'-fluoroacetophenone (Aldrich) in one portion. The mixture was stirred at ambient temperature for 1 hour and then cooled to 0° C.; another 75 mmol of sodium hydride was added and the resulting mixture stirred at ambient temperature for 15 minutes (or until the gas evolution has ceased). The reaction was recooled to −20° C. and treated with 19.1 g (69 mmol) of 2-bromo-4'-(methylsulfonyl)acetophenone (prepared in Step 3). The reaction was stirred at room temperature for 2 hours and concentrated in vacuo. The residue was partitioned between water and ethyl acetate; the ethyl acetate phase was dried (MgSO$_4$) and reconcentrated in vacuo. The residue was chromatographed on silica gel to give 13.8 g (51%) of dimethyl 2-[2-(4-fluorophenyl)-2-oxoethyl]-2-[2[-4-(methylsulfonyl)phenyl]-2-oxoethyl]propanedioate as an oil: NMR (CDCl$_3$) δ3.06 (s, 3H), 3.76 (s, 6H), 4.03 (s, 2H), 4.08 (s, 2H), 7.13 (t, J=8.6 Hz, 2H), 7.97–8.05 [m with d at 8.03 (J=8.7 Hz), 4H], 8.14 (d, J=8.5 Hz, 2H).

To a vigorously stirred mixture of 50.4 g (771 mmol) of zinc dust in 640 mL of THF at −78° C. under an atmosphere of nitrogen was added dropwise 60.4 mL (551 mmol) of titanium(IV) chloride. The reaction was warmed to ambient temperature with a water bath and then stirred at reflux for 1 hour. To the resulting dark mixture under reflux was added a solution of 15 g (32.3 mmol) of dimethyl 2-[2-(4-fluorophenyl)-2-oxoethyl]-2-[2-[4-(methylsulfonyl)phenyl]-2-oxoethyl]propanedioate (prepared above) in 20 mL of THF. The resulting mixture was stirred at ambient temperature for 16 hours, filtered through a pad of celite, rinsed with ethyl acetate, and concentrated in vacuo. The residue was partitioned between water and ethyl acetate; the organic phase was washed with brine, dried (MgSO$_4$), and concentrated in vacuo. The residue was chromatographed on silica gel to give 6.26 g (44%) of 1-[2-(4-fluorophenyl)-4,4-dicarbomethoxycyclopenten-1-yl]-4-(methylsulfonyl)benzene which was identical to the material prepared in Step 8, Method A.

Step 9

Preparation of 1-[2-(4-fluorophenyl)-4,4-di(hydroxymethyl)cyclopenten-1-yl]-4-(methylsulfonyl)benzene Under nitrogen, a solution of 1.01 g (2.34 mmol) of 1-[2-(4-fluorophenyl)-4,4-dicarbomethoxycyclopenten-1-yl]-4-(methylsulfonyl)benzene (prepared in Step 8) in 1.5 mL of THF at −78° C. was treated with 11.6 mL (11.6 mmol) of DIBAL (1.0M in THF). The reaction was stirred at ambient temperature for 1.5 hours, quenched with acetone and aqueous NaOH, extracted with ethyl acetate, dried (MgSO$_4$), and concentrated in vacuo to give 840 mg of crude 1-[2-(4-fluorophenyl)-4,4-di(hydroxymethyl)

cyclopenten-1-yl]-4 -(methylsulfonyl) benzene as a colorless oil: NMR (CDCl$_3$) δ2.82 (d, J=5 Hz, 4H), 3.04 (s, 3H), 3.86 (d, J=5 Hz, 4H), 6.94 (t, J=9 Hz, 2H), 7.11 (dd, J=5 and 9 Hz, 2H), 7.33 (d, J=9 Hz, 2H), 7.77 (d, J=9 Hz, 2H).

Step 10

Preparation of 1-[2-(4-fluorophenyl)-4,4-di(tosylmethyl)cyclopenten-1-yl]-4-(methylsulfonyl) benzene Under nitrogen, a solution of 2.34 mmol of the crude 1-[2-(4-fluorophenyl)-4,4-di(hydroxymethyl)cyclopenten-1-yl]-4-(methylsulfonyl)benzene (prepared in Step 9) in 8 mL of pyridine at ambient temperature was treated with 1.2 g (6.3 mmol) of p-toluenesulfonyl chloride (tosyl chloride). The resulting solution was stirred at room temperature for 17 hours, concentrated in vacuo, and chromatographed on silca gel to give 1.06 g (66% overall yield from Step 9) of 1-[2-(4-fluorophenyl)-4,4-di(tosylmethyl)cyclopenten-1-yl]-4-(methylsulfonyl)benzene as a colorless solid: NMR (CDCl$_3$) δ2.46 (s, 6H), 2.73 (s, 3H), 3.04 (s, 3H), 4.05 (s, 4H), 6.85–7.0 (m, 4H), 7.20 (d, J=8 Hz, 2H), 7.34 (d, J=8 Hz, 4H), 7.75 (d, J=8 Hz, 6H).

Step 11

Preparation of 5-(4-fluorophenyl)-6-[4-(methylsulfonylphenyl]spiro[2.4]hept-5-ene Under nitrogen, a solution of 1.02 g (1.49 mmol) of 1-[2-(4-fluorophenyl)-4,4-di(tosylmethyl)cyclopenten-1-yl]-4-(methylsulfonyl)benzene (prepared in Step 10) in 24 mL of DMF was treated with 3.23 g (21.55 mmol) of sodium iodide and 1.61 g (24.63 mmol) of zinc dust. The reaction was stirred an 150° C. for 1.5 hours, concentrated in vacuo, and partitioned between water and ethyl acetate. The organic phase was washed with sodium sulfite, water, brine, dried (MgSO$_4$), and concentrated in vacuo. The residue was chromatographed on silica gel to give 437 mg (86%) of 5-(4-fluorophenyl)-6-[4-(methylsulfonyl)phenyl]spiro[2.4]hept-5-ene as a colorless solid: mp 140.5°–142.0° C.; NMR (CDCl$_3$) δ0.69 (s, 4H), 2.92 (s, 4H), 3.04 (s, 3H), 6.93 (t, J=9 Hz, 2H), 7.10 (dd, J=5 and 9 Hz, 2H), 7.32 (d, J=8 Hz, 2H), 7.76 (d, J=8 Hz, 2H). HRMS. Calc'd for C$_{20}$H$_{19}$FO$_2$S: 342.1090. Found: 342.1126. Anal. Calc'd for C$_{20}$H$_{19}$FO$_2$S: C, 70.15; H, 5.59; F, 5.55; S, 9.36. Found: C, 70.10; H, 5.69; F, 5.50; S, 9.60.

Step 12

Preparation of 5-(4-fluorophenyl)-6-[4-(methylsulfonyl)phenyl]spiro[2.4]hepta-4,6

A solution of 500 mg (1.46 mmol) of 5-(4-fluorophenyl)-6-[4-(methylsulfonyl)phenyl]spiro[2.4]hept-5-ene (from Step 11) in 7 mL of dichloromethane was treated with 480 mg (55% peroxyacid, 1.53 mmol) of m-chloroperoxybenzoic acid (MCPBA). The reaction was stirred at ambient temperature for 2.5 hours, washed with aqueous saturated sodium bisulfite, dried (MgSO$_4$), and concentrated in vacuo to give a mixture of desired expoxide intermediate and m-chlorobenzoic acid; this crude mixture in 10 mL of acetic acid and 1 mL of water was subsequently treated with 500 mg (6.1 mmol) of sodium acetate and stirred at 80° C. for 10 hours. The reaction mixture was cooled to ambient temperature and concentrated in vacuo. The residue was partitioned between water and ethyl acetate; the organic phase was washed with aqueous saturated sodiun bicarbonate, water, brine, dried (MgSO$_4$), and reconcentrated in vacuo. Purification by silica gel chromatography gave 317 mg (64%) of 5-(4-fluorophenyl)-6-[4-(methylsulfonyl)phenyl]spiro[2.4]hepta-4,6-diene as a colorless solid: mp 119°–128° C. (dec); NMR (CDCl$_3$) δ1.81 (s, 4H), 3.06 (s, 3H), 6.22 (d, J=2 Hz, 1H), 6.36 d, J=2 Hz, 1H), 6.95 (t, J=8 Hz, 2H), 7.02–7.18 (m, 2H), 7.33 (d, J=8 Hz, 2H), 7.80 (d, J=8 Hz, 2H). MS (FAB) m/e (rel intensity) 347 (100) (M+Li). HRMS. Calc'd for C$_{20}$H$_{17}$FO$_2$S: 340.0933. Found: 340.0952. Anal. Calc'd for C$_{20}$H$_{17}$FO$_2$S: C, 69.29; H, 4.97; F, 5.45. Found: C, 69.21; H, 5.23; F, 5.81.

EXAMPLE 2

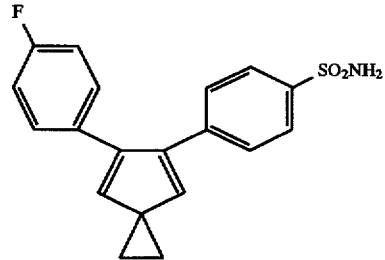

4-[6-(4-Fluorophenyl)spiro[2.4]hepta-4,6dien-5-yl]benzenesulfonamide

Step 1

Preparation of 4-[6-(4-fluorophenyl) spiro[2.4]hept-5-en-5-yl]benzenesulfonamide Under nitrogen, a solution of 90 mg (0.248 mmol) of 5-(4-fluoro phenyl)-6-[4-(methylsulfonyl)phenyl]spiro[2.4]hept-5-ene (the title compound of Example 1) in 1 mL of THF at −78° C. was treated with 0.21 mL (0.27 mmol) of methyllithium (1.3M in ether) over a period of 2 minutes. The reaction was stirred at ambient temperature for 25 minutes, cooled to −78° C., and treated with 0.3 mL (0.3 mmol) of tributylborane (1.0M in THF). The resulting dark brown solution was stirred at ambient temperature for 20 minutes and then at reflux for 16 hours prior to the addition of 350 mg (4.27 mmol) of sodium acetate, 2 mL of water, and 250 mg (2.21 mmol) of hydroxyamine-O-sulfonic acid. The resulting light orange mixture was stirred at ambient temperature for 3 hours and the aqueous phase extracted with ethyl acetate. The combined extracts were washed with water, brine, dried (MgSO$_4$), and concentrated in vacuo. The residue was chromatographed on silica gel to give 24 mg (27%) of 4-[6-(4-fluoro phenyl)spiro[2.4]hept-5-en-5-yl] benzenesulfonamide as a colorless solid: mp 131.0°–133.0° C.; NMR (CDCl$_3$) δ0.68 (s, 4H), 2.90 (s, 3H), 4.81 (s, 2H), 6.92 (t, J=9 Hz, 2H), 7.11 (dd, J=6 and 9 Hz, 2H), 7.27 (d, J=9 Hz, 2H), 7.74 (d, J=9 Hz, 2H). HRMS. Calc'd for C$_{19}$H$_{18}$FNO$_2$S: 344.1121. Found: 344.1122. Anal. Calc'd for [C$_{19}$H$_{18}$FNO$_2$S+0.1 CH$_3$CO$_2$CH$_2$CH$_3$]: C, 66.16; H, 5.38; N, 3.98; S, 9.11. Found: C, 65.86; H, 5.52; N, 3.92; S, 9.57.

Step 2

Preparation of 4-[6-(4-fluorophenyl) spiro[2.4]hepta-4,6-dien-5-yl]benzenesulfonamide A solution of 300 mg (0.88 mmol) of 4-[6-(4-fluorophenyl)spiro[2.4]hept-5-en-5-yl]benzenesulfonamide (from Step 1) in 5 mL of dichloromethane was treated with 300 mg (55% peroxyacid, 0.96 mmol) of m-chloroperoxybenzoic acid (MCPBA). The reaction was stirred at ambient temperature for 2.5 hours, washed with aqueous saturated sodium bisulfite, dried (MgSO$_4$), and concentrated in vacuo to give a mixture of desired expoxide intermediate and m-chlorobenzoic acid; this crude mixture in 6 mL of acetic acid and 0.6 mL of water was subsequently treated with 300 mg (3.7 mmol) of sodium acetate and stirred at 80° C. for 10 hours. The reaction mixture was cooled to ambient temperature and concentrated in vacuo. The residue was partitioned between water and ethyl acetate; the organic phase was washed with aqueous saturated sodium bicarbonate, water, brine, dried (MgSO$_4$), and reconcentrated in vacuo. Purification by silica gel chromatography gave 118 mg (39%) of 4-[6-(4-fluorophenyl)spiro [2.4]hepta-4,6-dien-5-yl]benzenesulfonamide as a colorless solid: mp 110°–116° C. (dec); NMR (CDCl$_3$) δ1.80 (s, 4H), 4.81 (br s, 2H), 6.21 (d, J=2 Hz, 1H), 6.33 (d, J=2 Hz, 1H), 6.94 (t, J=9 HZ, 2H), 7.06–7.15 (m, 2H), 7.29 d, J=8 Hz, 2H), 7.78 (d, J=8 Hz, 2H),

BIOLOGICAL EVALUATION

Rat Carrageenan Foot Pad Edema Test

The carrageenan foot edema test was performed with materials, reagents and procedures essentially as described by Winter, et al. (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in *Non-steroidal Anti-Inflammatory Drugs*, (J. Lombardino, ed. 1985)). Results are shown in Table L Rat Carrageenan-induced Analgesia Test The rat carrageenan analgesia test was performed with materials, reagents and procedures essentially as described by Hargreaves, et al. (*Pain*, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table L

TABLE I

| | RAT PAW EDEMA % Inhibition @ 30 mg/kg body weight | ANALGESIA % Inhibition @ 10 mg/kg body weight |
|---|---|---|
| Example 1 | 49 | 94 |

Evaluation of COX I and COX II activity

The compounds of this invention exhibited inhibition in vitro of COX II. The COX II inhibition activity of the compounds of this invention illustrated in the Examples was determined by the following methods.

a. Preparation of recombinant cox baculoviruses

A 2.0 kb fragment containing the coding region of either human or murine COX-I or human or murine COX-II was cloned into a BamH1 site of the baculovirus transfer vector pVL1393 (Invitrogen) to generate the baculovirus transfer vectors for COX-I and COX-II in a manner similar to the method of D. R. O'Reilly et al (*Baculovirus Expression Vectors: A Laboratory Manual* (1992)). Recombinant baculoviruses were isolated by transfecting 4 μg of baculovirus transfer vector DNA into SF9 insect cells (2×10$^6$/ml) along with 200 ng of linearized baculovirus plasmid DNA by the calcium phosphate method. See M. D. Summers and G. E. Smith, *A Manual of Methods for Baculovirus Vectors and Insect Cell Culture Procdures*. Texas Agric. Exp. Station Bull. 1555 (1987). Recombinant viruses were purified by three rounds of plaque purification and high titer (10E7–10E8 pfu/ml) stocks of virus were prepared. For large scale production, SF9 insect cells were infected in 10 liter fermentors (0.5×10$^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000xG for 30 minutes, and the resultant supernatant was stored at −80° C. before being assayed for COX activity.

b. Assay for COX I and COX II activity:

COX activity was assayed as PGE2 formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The PGE$_2$ formed was measured by standard ELISA technology (Cayman Chemical). Results are shown in Table II.

TABLE II

| | COX I ID$_{50}$ μM | COX II ID$_{50}$ μM |
|---|---|---|
| Example 1 | 1.3 | <.1 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

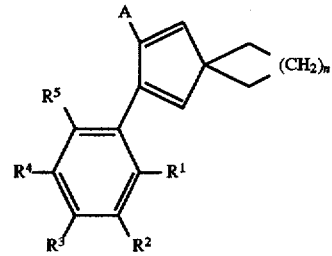

wherein A is selected from

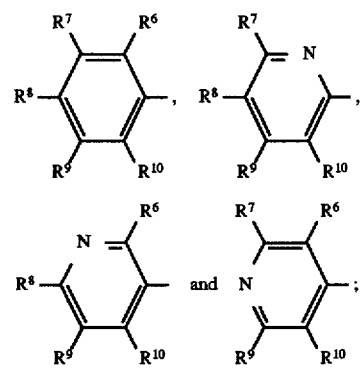

wherein each of $R^1$ through $R^{10}$ is independently selected from hydrido, halo, alkyl, alkoxy, alkylthio, cyano, haloalkyl, haloalkoxy, hydroxyalkyl, alkoxyalkyl, hydroxyl, mercapto, alkylsulfonyl, haloalkylsulfonyl and sulfamyl; and wherein n is a number selected from 0, 1, 2 and 3; or a pharmaceutically-acceptable salt thereof.

2. A compound of Formula II

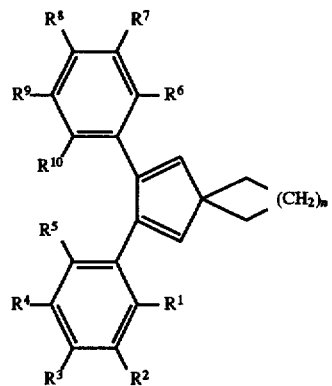

wherein each of $R^1$, $R^2$, $R^4$ and $R^5$ is hydrido; wherein $R^3$ is methylsulfonyl or sulfamyl; and wherein each of $R^6$ through $R^{10}$ is independently selected from hydrido, halo, alkyl, alkoxy, alkylthio, cyano, haloalkyl, haloalkoxy, hydroxyalkyl, alkoxyalkyl, hydroxyl, and mercapto; and wherein n is 1, 2 or 3; or a pharmaceutically-acceptable salt thereof.

3. Compound of claim 2 wherein n is 1, 2 or 3; and wherein each of $R^6$ through $R^{10}$ is independently selected from hydrido, halo, lower alkyl, lower alkylthio, cyano, lower haloalkyl, lower haloalkoxy, lower alkoxy, hydroxyl, mercapto, lower hydroxyalkyl, and lower alkoxyalkyl; or a pharmaceutically-acceptable salt thereof.

4. Compound of claim 3 wherein n is 1 or 2; and wherein each of $R^6$ through $R^{10}$ is independently selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl, and ethoxymethyl; or a pharmaceutically-acceptable salt thereof.

5. Compound of claim 4 selected from compounds, and their pharmaceutically-acceptable salts, of the group consisting of
6-phenyl-7-[4-(methylsulfonyl)phenyl]spiro[3.4]octa-5,7-diene;
6-(4-fluorophenyl)-7-[4-(methylsulfonyl)phenyl]spiro[3,4]octa-5,7-diene;
6-(4-chlorophenyl)-7-[4-(methylsulfonyl)phenyl]spiro[3,4]octa-5,7-diene;
6-(4-methylphenyl)-7-[4-(methylsulfonyl)phenyl]spiro[3,4]octa-5,7-diene;
6-(4-methoxyphenyl)-7-[4-(methylsulfonyl)phenyl]spiro[3,4]octa-5,7-diene;
6-(4-methylthiophenyl)-7-[4-(methylsulfonyl)phenyl]spiro[3,4]octa-5,7-diene;
6-(4-cyanophenyl)-7-[4-(methylsulfonyl)phenyl]spiro[3,4]octa-5,7-diene;
6-(4-trifluoromethylphenyl)-7-[4-(methylsulfonyl) phenyl]spiro[3.4]octa-5,7-diene;
4-(7-phenylspiro[3.4]octa-5,7-dien-6-yl) benzenesulfonamide;
4-[7-4-fluorophenyl)spiro[3.4]octa-5,7-dien-6-yl] benzenesulfonamide;
4-[7-4-chlorophenyl)spiro[3.4]octa-5,7-dien-6-yl] benzenesulfonamide;
4-[7-4-methylphenyl)spiro[3.4]octa-5,7-dien-6-yl] benzenesulfonamide;
4-[7-4-methoxyphenyl)spiro[3.4]octa-5,7-dien-6-yl] benzenesulfonamide;
4-[7-4-methylthiophenyl)spiro[3.4]octa-5,7-dien-6-yl] benzenesulfonamide;
4-[7-4-cyanophenyl)spiro[3.4]octa-5,7-dien-6-yl] benzenesulfonamide;
4-[7-(4-trifluoromethylphenyl)spiro[3.4]octa-5,7-dien-6-yl] benzenesulfonamide;
2-phenyl-3-[4-(methylsulfonyl)phenyl]spiro[4.4]nona-1,3-diene;
2-(4-fluorophenyl)-3-[4-(methylsulfonyl)phenyl]spiro[4.4]nona-1,3-diene;
2-(4-chlorophenyl)-3-[4-(methylsulfonyl)phenyl]spiro[4.4]nona-1,3-diene;
2-(4-methylphenyl)-3-[4-(methylsulfonyl)phenyl]spiro[4.4]nona-1,3-diene;
2-(4-methoxyphenyl)-3-[4-(methylsulfonyl)phenyl]spiro[4.4]nona-1,3-diene;
2-(4-methylthiophenyl)-3-[4-(methylsulfonyl) phenyl]spiro[4.4]nona-1,3-diene;
2-(4-cyanophenyl)-3-[4-(methylsulfonyl)phenyl]spiro[4.4]nona-1,3-diene;
2-(4-trifluoromethylphenyl)-3-[4-(methylsulfonyl) phenyl]spiro[4.4]nona-1,3-diene;
4-(3-phenylspiro[4.4]nona-1,3-dien-2-yl) benzenesulfonamide;
4-[3-(4-fluorophenyl)spiro[4.4]nona-1,3-dien-2-yl] benzenesulfonamide;
4-[3-(4-chlorophenyl)spiro[4.4]nona-1,3-dien-2-yl] benzenesulfonamide;
4-[3-(4-methylphenyl)spiro[4.4]nona-1,3-dien-2-yl] benzenesulfonamide;
4-[3-(4-methoxyphenyl)spiro[4.4]nona-1,3-dien-2-yl] benzenesulfonamide;
4-[3-(4-methylthiophenyl)spiro[4.4]nona-1,3-dien-2-yl] benzenesulfonamide;
4-[3-(4-cyanophenyl)spiro[4.4]nona-1,3-dien-2-yl] benzenesulfonamide; and
4-[3-(4-trifluoromethylphenyl)spiro[4.4]nona-1,3-dien-2-yl]benzenesulfonamide.

6. A pharmaceutical composition comprising a therapeutically effective amount of a compound, said compound selected from a family of compounds of claim 2; or a pharmaceutically-acceptable salt thereof.

7. A pharmaceutical composition comprising a therapeutically effective amount of a compound, said compound selected from a family of compounds of claim 3, or a pharmaceutically-acceptable salt thereof.

8. A pharmaceutical composition comprising a therapeutically effective amount of a compound, said compound selected from a family of compounds of claim 4; or a pharmaceutically-acceptable salt thereof.

9. A pharmaceutical composition comprising a therapeutically effective amount of a compound, said compound selected from a family of compounds of claim 5; or a pharmaceutically-acceptable salt thereof.

10. A method of treating inflammation or an inflammation-associated disorder in a subject, said method comprising administering to the subject having such inflammation or inflammation-associated disorder, a therapeutically effective amount of a compound of claim 2; or a pharmaceutically-acceptable salt thereof.

11. A method of treating inflammation or an inflammation-associated disorder in a subject, said method comprising administering to the subject having such inflammation or inflammation-associated disorder, a therapeutically effective amount of a compound of claim 3; or a pharmaceutically-acceptable salt thereof.

12. A method of treating inflammation or an inflammation-associated disorder in a subject, said method comprising administering to the subject having such inflammation or inflammation-associated disorder, a therapeutically effective amount of a compound of claim 4; or a pharmaceutically-acceptable salt thereof.

13. A method of treating inflammation or an inflammation-associated disorder in a subject, said method comprising administering to the subject having such inflammation or inflammation-associated disorder, a therapeutically effective amount of a compound of claim 5; or a pharmaceutically-acceptable salt thereof.

14. The method of claim 10 for treatment of inflammation.

15. The method of claim 10 for treatment of an inflammation-associated disorder.

16. The method of claim 15 wherein the inflammation-associated disorder is arthritis.

17. The method of claim 15 wherein the inflammation-associated disorder is pain.

18. The method of claim 15 wherein the inflammation-associated disorder is fever.

* * * * *